United States Patent
Booker et al.

(10) Patent No.: US 7,759,344 B2
(45) Date of Patent: Jul. 20, 2010

(54) BIS-ARYL AMIDE DERIVATIVES AND METHODS OF USE

(75) Inventors: Shon Booker, Thousand Oaks, CA (US);
Noel D'Angelo, Thousand Oaks, CA (US); Julie Germain, Quebec (CA);
Jean-Christophe Harmange, Andover, MA (US); Tae-Seong Kim, Thousand Oaks, CA (US); Michele Potashman, Cambridge, MA (US)

(73) Assignee: Amgen Inc., Thousand Oaks, CA (US)

( * ) Notice: Subject to any disclaimer, the term of this patent is extended or adjusted under 35 U.S.C. 154(b) by 29 days.

(21) Appl. No.: 12/008,241

(22) Filed: Jan. 9, 2008

(65) Prior Publication Data

US 2008/0234268 A1   Sep. 25, 2008

Related U.S. Application Data

(60) Provisional application No. 60/879,671, filed on Jan. 9, 2007.

(51) Int. Cl.
*A61K 31/495* (2006.01)
*A61K 31/4725* (2006.01)
*A61K 31/416* (2006.01)
*C07D 487/04* (2006.01)
*C07D 217/00* (2006.01)
*C07D 231/54* (2006.01)

(52) U.S. Cl. .................. 514/248; 514/310; 514/405; 544/236; 546/143; 548/362.1

(58) Field of Classification Search .................. 544/236; 546/143; 548/362.1; 514/248, 310, 405
See application file for complete search history.

(56) References Cited

FOREIGN PATENT DOCUMENTS

| WO | WO 05/116028 | 12/2005 |
| WO | WO 07/115408 | 10/2007 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Kaufmann et al., "Uber die 1-Phenyl-2, 3-dimethyl-pyrazolon-(5)-carbonsaure-(4) (Antipyrinsaure) und Ihre Abkommlinge", Berichte Der Deutschen Chemischen Gesellschaft Abteilung B: Abhandlungen, 1214-1236 (1942).

* cited by examiner

*Primary Examiner*—Kamal A Saeed
*Assistant Examiner*—Samantha L Shterengarts

(57) ABSTRACT

Selected compounds are effective for prophylaxis and treatment of diseases, such as c-Met mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

12 Claims, No Drawings

BIS-ARYL AMIDE DERIVATIVES AND METHODS OF USE

This application claims priority to U.S. Provisional Application Ser. No. 60/879,671 filed Jan. 9, 2007 the entirety of which is incorporated herein by reference.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins, which play a central role in the regulation of a wide variety of cellular processes, maintaining control over cellular function. A partial list of such kinases includes ab1, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ron ros, tie, tie2, TRK, Yes, and Zap70. Inhibition of such kinases has become an important therapeutic target.

The hepatocyte growth factor receptor ("c-Met") is a unique receptor tyrosine kinase shown to be over expressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Over expression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met proto-oncogene have been postulated to play a role in microglial reactions to CNS injuries (Oncogene, 8:219-222 (1993)).

Metastatic SCC cells overexpress c-Met and have enhanced tumoregenesis and metastasis in vivo [G. Gong et al., Oncogene, 23:6199-6208 (2004)]. C-Met is required for tumor cell survival [N. Shinomiya et al., Cancer Research, 64:7962-7970 (2004)]. For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Compounds of the current invention are inhibitors of c-Met.

DESCRIPTION OF THE INVENTION

A class of compounds useful in treating cancer and angiogenesis as defined by Formulae I, II and III.

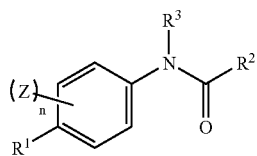

I

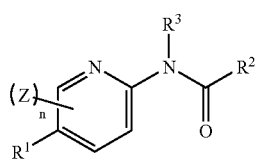

II

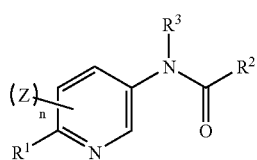

III enantiomers, diastereomers, salts and solvates thereof wherein $R^1$ is an aryl ring system or a 5-14-membered nitrogen containing heteroaryl or heterocyclyl ring system; any of which may be optionally independently substituted with 1 to 4 Z groups;

$R^2$ is

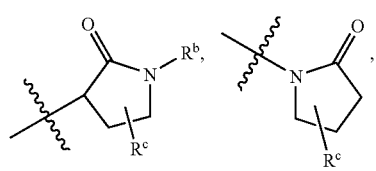

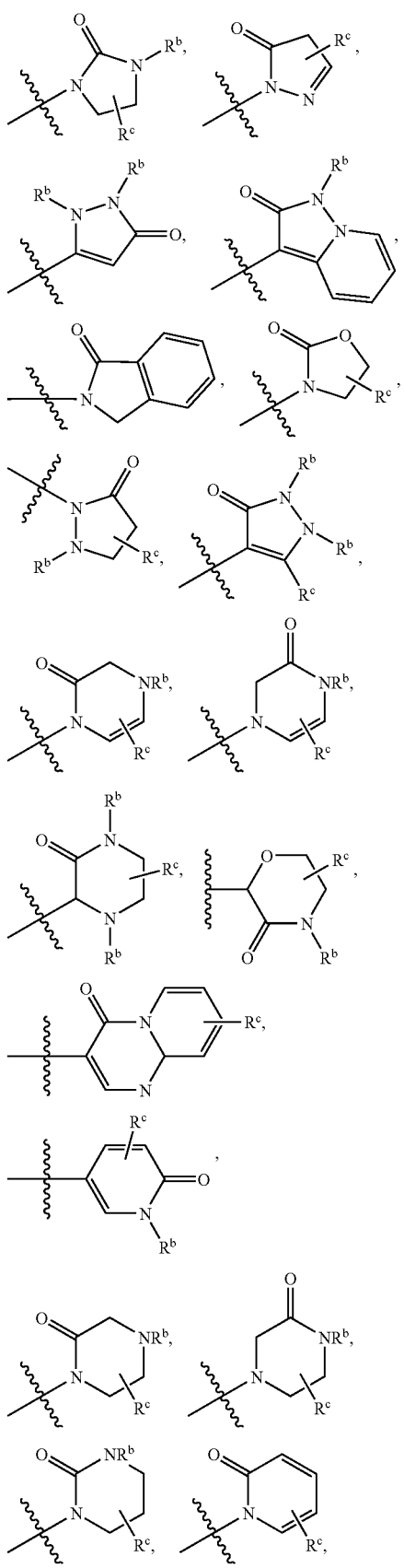

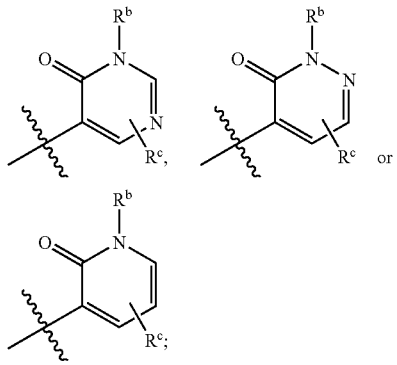

R³ is hydrogen or alkyl optionally substituted with one or more Z groups;

R$^b$ is independently selected at each occurrence from
  a) H, or
  b) C$_{1-6}$alkyl, C$_{3-6}$cycloalkyl, C$_{6-10}$ aryl, C$_{6-10}$ aryl-C$_{1-3}$ alkyl, C$_{5-10}$ heteroaryl, C$_{5-10}$ heteroaryl-C$_{1-3}$ alkyl, 5-6 membered heterocyclyl or 5-6-membered heterocyclyl-C$_{1-3}$ alkyl, any of which may be optionally substituted with one or more Z groups;

R$^c$ is selected from
  a) H, halo, hydroxy or
  b) C$_{1-6}$alkyl, C$_{3-6}$cycloalkyl, C$_{3-6}$cycloalkylC$_{1-6}$alkyl, C$_{1-6}$alkoxy, C$_{1-6}$alkyoxyC$_{1-6}$alkyl, hydroxy-C$_{1-6}$alkyl, C$_{6-10}$ aryl, C$_{6-10}$ aryl-C$_{1-3}$ alkyl, C$_{5-10}$ heteroaryl, C$_{5-10}$ heteroaryl-C$_{1-3}$ alkyl, 5-6 membered heterocyclyl, 5-6-membered heterocyclyl-C$_{1-3}$ alkyl, R$^d$R$^e$N— or R$^d$R$^e$N—C$_{1-3}$ alkyl, any of which may be optionally substituted with one or more Z groups;

R$^d$ is selected from
  a) H, or
  b) C$_{1-6}$alkyl, C$_{3-6}$cycloalkyl, C$_{3-6}$cycloalkylC$_{1-6}$alkyl, C$_{1-6}$alkyoxyC$_{1-6}$alkyl, hydroxy-C$_{1-6}$alkyl, C$_{6-10}$ aryl-C$_{1-3}$ alkyl, C$_{5-10}$ heteroaryl-C$_{1-3}$ alkyl, or 5-6-membered heterocyclyl-C$_{1-3}$ alkyl, any of which may be optionally substituted with one or more Z groups;

R$^e$ is selected from
  a) H or
  b) C$_{1-6}$alkyl, C$_{6-10}$ aryl-C$_{1-3}$ alkyl, 5-6 membered heterocyclyl-C$_{1-2}$-alkyl, 5-6-membered heterocyclyl; C$_{6-10}$ aryl, C$_{5-10}$ heteroaryl, or C$_{5-10}$ heteroaryl-C$_{1-3}$ alkyl, any of which may be optionally substituted with one or more Z groups;

or when R$^d$ and R$^e$ are bonded to the same nitrogen atom, they may optionally combine to form a heterocyclyl ring.

Z is an optional substituent independently selected at each occurance from
  a*) halo, nitrile, hydroxy, alkoxy, aryloxy, heteroaryloxy; heterocylyloxy, cycloalkyloxy, aralkyloxy, heteraralkyloxy, heterocyclylalkoxy, cycloalkylalkoxy, —NR$^b$R$^b$, —NR$^b$—C(=O)R$^b$, —NR$^b$—C(=O)OR$^b$, —NR$^b$—C(=O)—NR$^b$R$^b$, —C(=O)—NR$^b$R$^b$, —C(=O)OR$^b$; —S(O$_2$)—NR$^b$R$^b$, —NR$^b$, —(SO$_2$)R$^b$, —S(O$_2$)R$^b$, and —S(O)R$^b$; or
  b*) alkyl, alkenyl, alkynyl, cycloalkyl, aryl, aralkyl, heteroaryl, heteroaralkyl, heterocyclyl, and heterocyclylalkyl, any of which may be optionally substituted with one or more of the substituents listed in the above section a*; and n is an integer from zero to three.

Preferred compounds of present invention include compounds wherein R² is

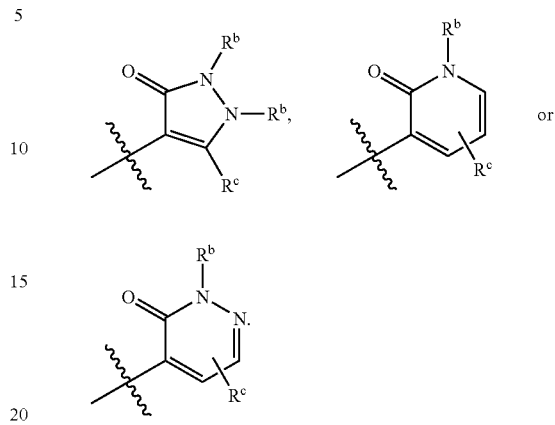

Preferred compounds of the present invention further include compounds wherein R² is

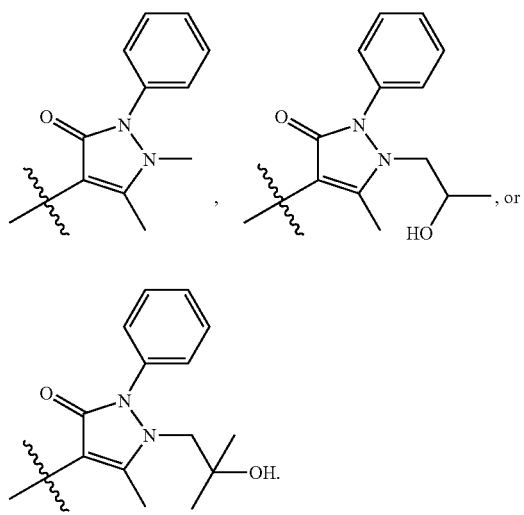

Preferred compounds of the present invention further include compounds wherein R¹ is

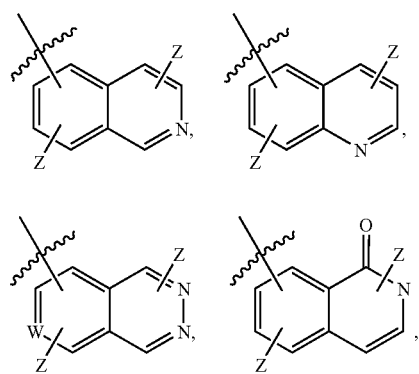

-continued

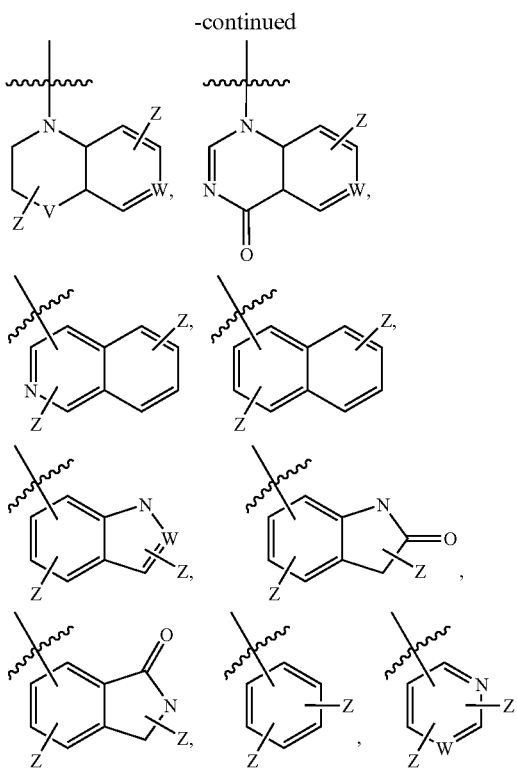

where W is C or N; and
V is C, O or N.

Preferred compounds of the present invention further include compounds wherein $R^1$ is

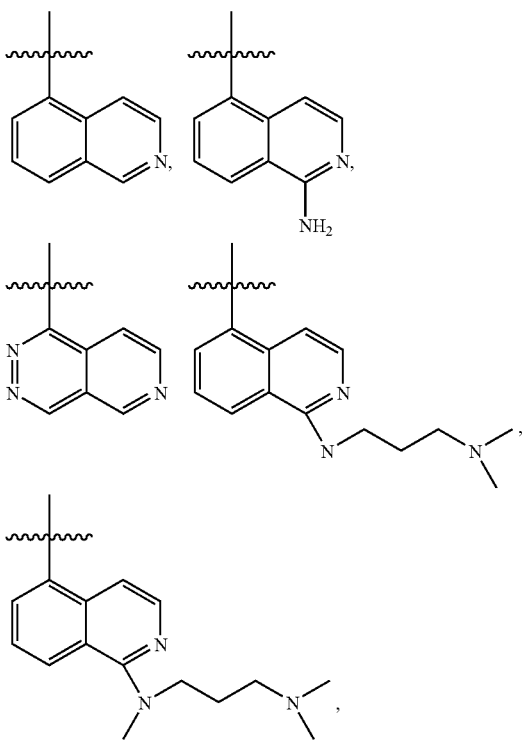

-continued

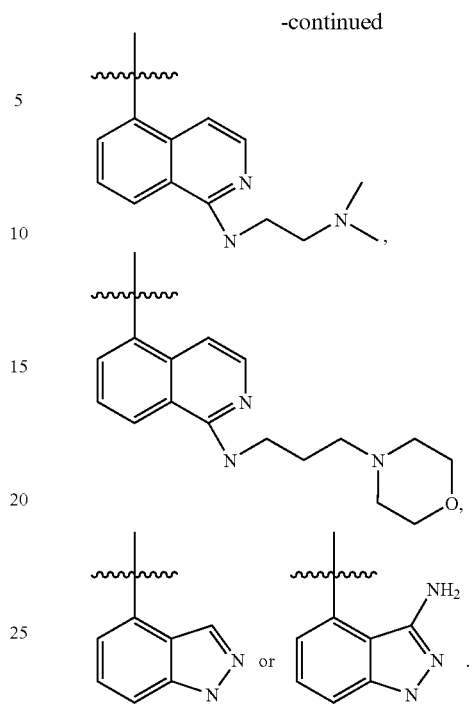

The invention also relates to pharmaceutical compositions containing the above compounds, together with a pharmaceutically acceptable vehicle or carrier.

The invention also relates to a method of treating cancer in a subject using the above compounds.

The invention also relates to a method of reducing tumor size in a subject using the above compounds.

The invention also relates to a method of reducing metastasis in a tumor in a subject, using the above compounds.

The invention also relates to a method of treating HGF-mediated disorders in a subject using the above compounds.

Indications

Compounds of the present invention would be useful for, but not limited to, the prevention or treatment of angiogenesis related diseases. The compounds of the invention have c-Met inhibitory activity. The compounds of the invention are useful in therapy as antineoplasia agents or to minimize deleterious effects of HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, lck, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

Definitions

"Angiogenesis" is defined as any alteration of an existing vascular bed or the formation of new vasculature, which benefits tissue perfasion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" (or "heterocyclo"} embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term heterocycly, (or heterocyclo) 1 also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I, II and III" includes any sub formulas.

The compounds of the invention are endowed with c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of c-Met.

The present invention comprises a pharmaceutical composition comprising a therapeutically effective amount of a compound of Formulas I, II, and III in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of Formula I, II, and IIII.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I, II and III may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;
2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;
N-[3-(Azetidin-3-ylmethoxy)-5-trifluoromethyl-phenyl]-2-(4-fluoro-benzylamino)-nicotinamide.
6-fluoro-N-(4-(1-methylethyl)phenyl)-2-((4-pyridinylmethyl)amino)-3-pyridinecarboxamide;
2-((4-pyridinylmethyl)amino)-N-(3-(((2S)-2-pyrrolidinylmethyl)oxy)-5-(trifluoromethyl)phenyl)-3-pyridinecarboxamide;
N-(3-(1,1-dimethylethyl)-1H-pyrazol-5-yl)-2-((4-pyridinylmethyl)amino)-3-pyridinecarboxamide;
N-(3,3-dimethyl-2,3-dihydro-1-benzofuran-6-yl)-2-((4-pyridinylmethyl)amino)-3-pyridinecarboxamide;
N-(3-((((2S)-1-methyl-2-pyrrolidinyl)methyl)oxy)-5-(trifluoromethyl)phenyl)-2-((4-pyridinylmethyl)amino)-3-pyridinecarboxamide;
2-((4-pyridinylmethyl)amino)-N-(3-((2-(1-pyrrolidinyl)ethyl)oxy)-4-(trifluoromethyl)phenyl)-3-pyridinecarboxamide;
N-(3,3-dimethyl-2,3-dihydro-1H-indol-6-yl)-2-((4-pyridinylmethyl)amino)-3-pyridinecarboxamide;
N-(4-(pentafluoroethyl)-3-(((2S)-2-pyrrolidinylmethyl)oxy)phenyl)-2-((4-pyridinylmethyl)amino)-3-pyridinecarboxamide;
N-(3-((3-azetidinylmethyl)oxy)-5-(trifluoromethyl)phenyl)-2-((4-pyridinylmethyl)amino)-3-pyridinecarboxamide;
N-(3-(4-piperidinyloxy)-5-(trifluoromethyl)phenyl)-2-((2-(3-pyridinyl)ethyl)amino)-3-pyridinecarboxamide;
N-(4,4-dimethyl-1,2,3,4-tetrahydro-isoquinolin-7-yl)-2-(1H-indazol-6-ylamino)-nicotinamide;
2-(1H-indazol-6-ylamino)-N-[3-(1-methylpyrrolidin-2-ylmethoxy)-5-trifluoromethyl-phenyl]-nicotinamide;
N-[1-(2-dimethylamino-acetyl)-3,3-dimethyl-2,3-dihydro-1H-indol-6-yl]-2-(1H-indazol-6-ylamino)-nicotinamide;
2-(1H-indazol-6-ylamino)-N-[3-(pyrrolidin-2-ylmethoxy)-5-trifluoromethyl-phenyl]-nicotinamide;
N-(1-acetyl-3,3-dimethyl-2,3-dihydro-1H-indol-6-yl)-2-(1H-indazol-6-ylamino)-nicotinamide;
N-(4,4-dimethyl-1-oxo-1,2,3,4-tetrahydro-isoquinolin-7-yl)-2-(1H-indazol-6-ylamino)-nicotinamide;
N-[4-(tert-butyl)-3-(3-piperidylpropyl)phenyl][2-(1H-indazol-6-ylamino)(3-pyridyl)]carboxamide;
N-[5-(tert-butyl)isoxazol-3-yl][2-(1H-indazol-6-ylamino)(3-pyridyl)]carboxamide; and
N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide.(Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055,(Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070);

ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TurnStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I, II and III.

Also included in the family of compounds of Formula I, II and III are the pharmaceutically acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of Formula I, II and III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I, II and III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I, II and, III. When a basic group and an acid group are present in the same molecule, a compound of Formula I, II and IIII may also form internal salts.

General Synthetic Procedures

The compounds of the invention can be synthesized according to the following procedures of Schemes 1-10, wherein the substituents are as defined for Formulas I, II and III above, except where further noted.

The following abbreviations are used throughout the specification:
HOAc—acetic acid
MeCN, $CH_3CN$—acetonitrile
$NH_3$—ammonia
$NH_4Cl$—ammonium chloride
Ar—argon
HBTA—O-benzotriazol-1-yl-N,N,N',N'-tetramethyluronium hexafluorophosphate
HATU—O-(7-azabenzotriazol-1-yl)-N,N,N',N'-tetramethyluronium hexafluorophosphate
PyBop—benzotriazol-1-yl-oxy-tripyrrolidino-phosphonium hexafluorophosphate
$Pd_2(dba)_3$—bis(dibenzylideneacetone) palladium
BINAP—2,2'-bis(diphenylphosphino)-1,1'-binaphthyl
TEAC—bis(tetra-ethylammonium)carbonate
$BBr_3$—boron tribromide
BSA—bovine serum albumin
$Br_2$—bromine
BOC—butyloxycarbonyl
$Cs_2CO_3$—cesium carbonate
$CHCl_3$—chloroform
$CDCl_3$—chloroform deuterated
Cu—copper
CuI—copper(I) iodide
$Et_2O$—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
$H_2$—hydrogen $H_2O_2$—hydrogen peroxide
Fe—iron
LiHMDS—lithium bis(trimethylsilyl)-amide
LDA—Lithium diisopropylamide
MCPBA—meta-chloroperbenzoic acid
$MgSO_4$—magnesium sulfate
MeOH, $CH_3OH$—methanol
MeI—methyl iodide
$CH_2Cl_2$, DCM—methylene chloride
NMP—N-methylpyrrolidinone
ML, ml—milliliter
$N_2$—nitrogen
Pd/C—palladium on carbon
$Pd(OAc)_2$—palladium acetate
$Pd(OH)_2$—palladium hydroxide
$Pd(PPh_3)_4$—palladium tetrakis triphenylphosphine
$Pd(dppf)Cl_2$—1-bis(diphenylphosphino)ferrocene palladium chloride
PBS—phosphate buffered saline
$POCl_3$—phosphorous oxychloride
$K_2CO_3$—potassium carbonate
KOH—potassium hydroxide
RT—room temperature
$NaHCO_3$—sodium bicarbonate
$NaBH_4$—sodium borohydride
$NaBH_3CN$—sodium cyanoborohydride
NaOtBu—sodium tert-butoxide
NaOH—sodium hydroxide
$NaClO_2$—sodium chlorite
NaCl—sodium chloride
$NaHPO_4$—sodium biphosphate
NaH—sodium hydride
NaI—sodium iodide
$Na_2SO_4$—sodium sulfate
TBTU—O-benzotriazol-1-yl-N,N,N',N'-tetramethyluronium tetrafluoroborate
THF—tetrahydrofuran
$Et_3N$, TEA—triethylamine
TFA—trifluoroacetic acid
$P(t-bu)_3$—tri(tert-butyl)phosphine
$H_2O$—water Although the pharmacological properties of the compounds of Formulas I, II and III vary with structural change, in general, activity possessed by compounds of Formulas I, II and III may be demonstrated in vivo. The pharmacological properties of the compounds of this invention may be confirmed by a number of pharmacological in vitro assays. The exemplified pharmacological assays, which follow have been carried out with the compounds according to the invention and their salts. Compounds of the present invention showed inhibition of c-Met kinase at doses less than 10 μM.

Scheme 1

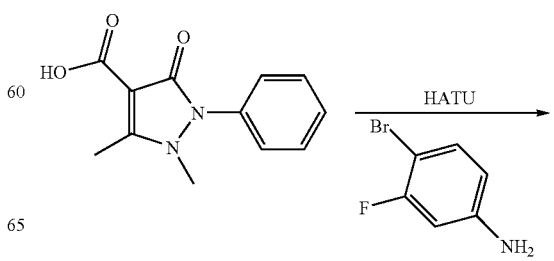

-continued

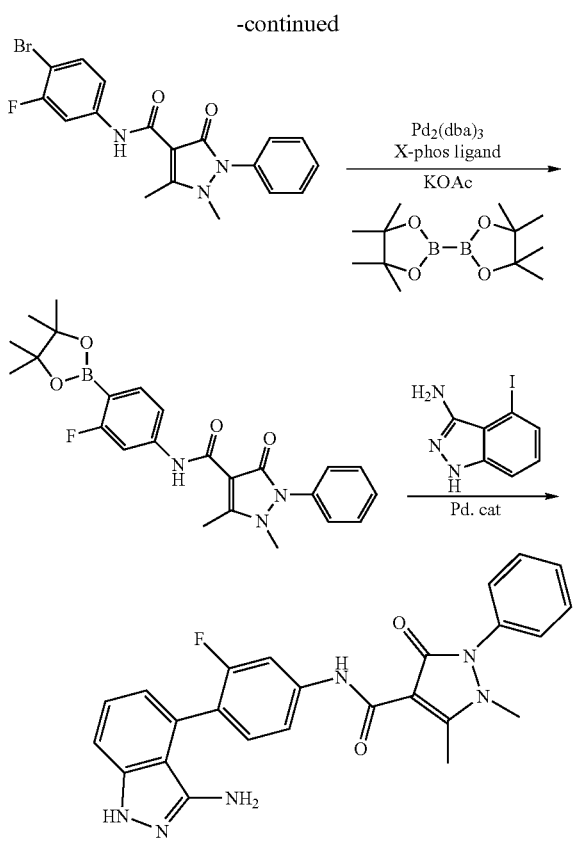

EXAMPLE 1

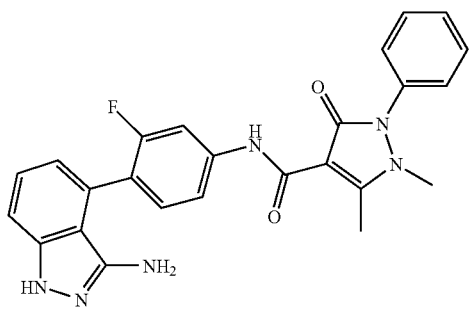

N-(4-(3-amino-1H-indazol-4-yl)-3-fluorophenyl)-1,5-dimethyl-3-oxo-2-phenyl-2,3-dihydro-1H-pyrazole-4-carboxamide. A sealable tube was charged with PdCl$_2$(dppf)-CH$_2$Cl$_2$ adduct (0.014 g, 0.017 mmol), N-(3-fluoro-4-(4,4,55-tetramethyl-1,3,2-dioxaborolan-2-yl)phenyl)-1,5-dimethyl-3-oxo-2-phenyl-2,3-dihydro-1H-pyrazole-4-carboxamide (0.150 g, 0.34 mmol), 4-iodo-1H-indazol-3-amine (0.089 g, 0.34 mmol), NaHCO$_3$ (0.38 ml, 0.75 mmol), dioxane (4.0 mL) and blanketed with nitrogen. The vessel was sealed and heated at 80° C. for 16 h. The mixture was allowed to cool to rt and diluted with ethyl acetate. The organic layer was washed with water and brine, dried over Na$_2$SO$_4$, filtered and evaporated. The mixture was purified via flash chromatography with an eluant of 0% to 10% methanol in ethyl acetate gradient. The title compound obtained as a tan solid (80 mg, 50%). MS (ESI pos. ion) m/z=457 (MH+). Calc'd mass for C$_{25}$H$_{21}$FN$_6$O$_2$: 456.48. $^1$H NMR (400 MHz, dmso-d$_6$) δ 11.74 (s, 1H), 11.01 (s, 1H), 7.85-7.88 (m, 1H), 7.58-7.62, 7.50-7.60 (m, 1H), 7.46 (d, J=7.45 Hz, 2H), 7.27-7.6 (m, 4H), 6.80-6.85 (m, 1H), 4.23 (s, 2H), 3.38 (s, 3H), 2.6 (s, 3H).

The compounds of Examples 2-9 were prepared using a protocol similar to Example 1:

EXAMPLE 2

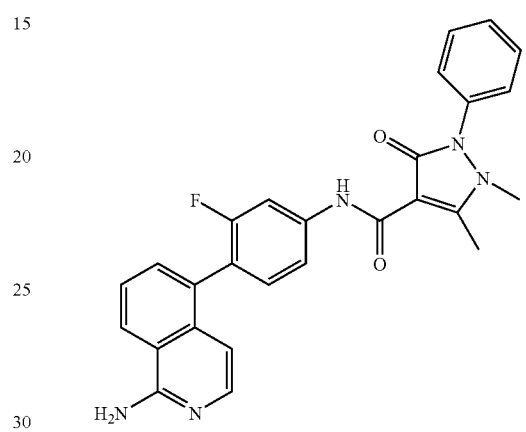

N-(4-(1-amino-5-isoquinolinyl)-3-fluorophenyl)-1,5-dimethyl-3-oxo-2-phenyl-2,3-dihydro-1H-pyrazole-4-carboxamide. MS (ESI pos. ion) m/z=468 (MH+). Calc'd mass for C$_{27}$H$_{22}$FN$_5$O$_2$: 467.49. $^1$H NMR (400 MHz, dmso-d$_6$) δ 11.07 (s, 1H), 8.25 (d, J=7.45, 1H), 7.86 (d, J=12 Hz, 1H), 7.76 (d, J=6.07 Hz, 1H), 7.58-7.62 (m, 2H), 7.50-7.55 (m, 3H), 7.45 (d, J=7.60 Hz, 2H), 7.30-7.35 (m, 2H), 6.89 (bs, 2H), 6.50-6.55 (m, 1H), 3.38 (s, 3H), 2.72 (s, 3H).

EXAMPLE 3

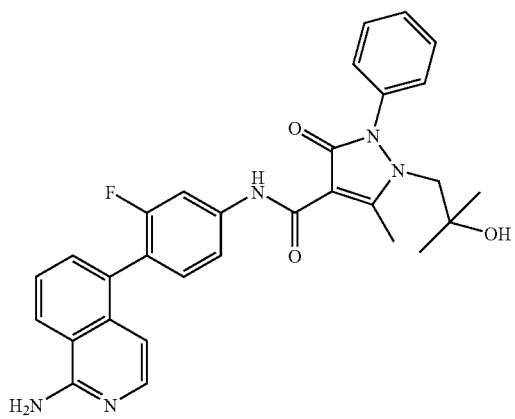

N-(4-(1-amino-5-isoquinolinyl)-3-fluorophenyl)-1-(2-hydroxy-2-methylpropyl)-5-methyl-3-oxo-2-phenyl-2,3-dihydro-1H-pyrazole-4-carboxamide. MS (ESI pos. ion) m/z=526 (MH+). Calc'd mass for C$_{30}$H$_{28}$FN$_5$O$_3$: 525.58.

EXAMPLE 4

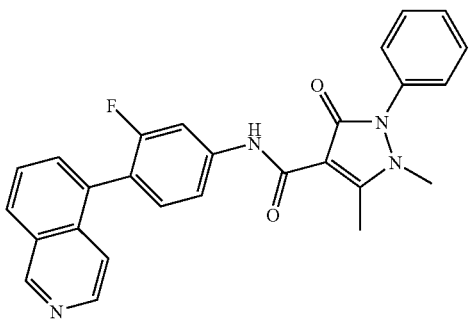

N-(3-fluoro-4-(5-isoquinolinyl)phenyl)-1,5-dimethyl-3-oxo-2-phenyl-2,3-dihydro-1H-pyrazole-4-carboxamide. MS (ESI pos. ion) m/z=453 (MH+). Calc'd mass for $C_{27}H_{21}FN_4O_2$: 452.48.

EXAMPLE 5

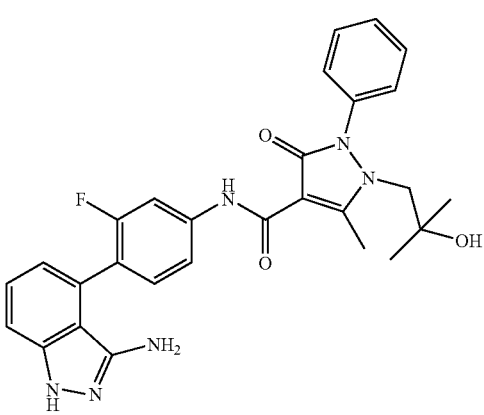

N-(4-(3-amino-1H-indazol-4-yl)-3-fluorophenyl)-1-(2-hydroxy-2-methylpropyl)-5-methyl-3-oxo-2-phenyl-2,3-dihydro-1H-pyrazole-4-carboxamide. MS (ESI pos. ion) m/z=515 (MH+). Calc'd mass for $C_{28}H_{27}FN_6O_3$: 514.56.

EXAMPLE 6

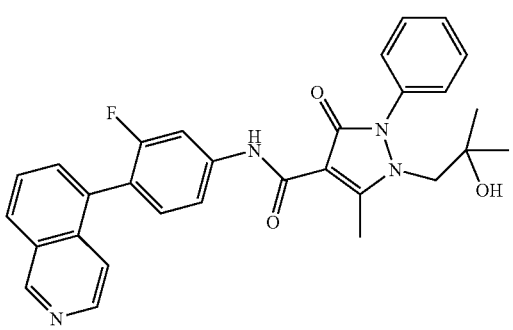

N-(3-fluoro-4-(5-isoquinolinyl)phenyl)-1-(2-hydroxy-2-methylpropyl)-5-methyl-3-oxo-2-phenyl-2,3-dihydro-1H-pyrazole-4-carboxamide. MS (ESI pos. ion) m/z=511 (MH+). Calc'd mass for $C_{30}H_{27}FN_4O_3$: 510.56. ¹H NMR (400 MHz, dmso-d₆) δ 11.04 (s, 1H), 9.40 (s, 1H), 8.50 (d, J=6.0, 1H), 8.18-8.22 (m, 1H), 7.94 (d, J=11.6 Hz, 1H), 7.75-7.78 (m, 2H), 7.53-7.60 (m, 2H), 7.40-7.50 (m, 4H), 7.36 (d, J=7.7 Hz, 2H), 3.30 (s, 2H), 2.81 (s, 3H), 0.97 (s, 6H).

EXAMPLE 7

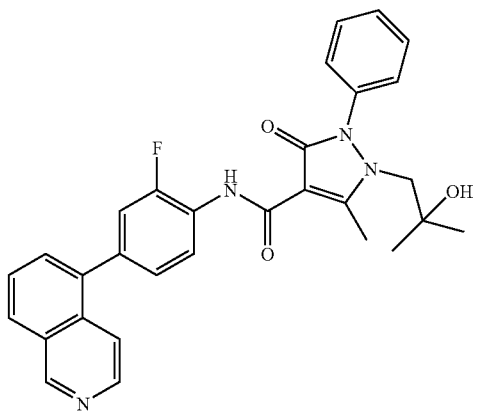

N-(2-fluoro-4-(5-isoquinolinyl)phenyl)-1-(2-hydroxy-2-methylpropyl)-5-methyl-3-oxo-2-phenyl-2,3-dihydro-1H-pyrazole-4-carboxamide. MS (ESI pos. ion) m/z=511 (MH+). Calc'd mass for $C_{30}H_{27}FN_4O_3$: 510.56.

EXAMPLE 8

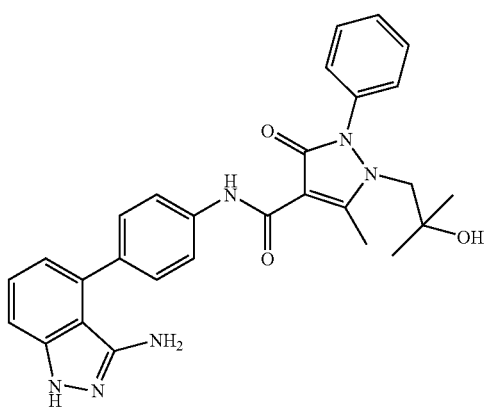

N-(4-(3-amino-1H-indazol-4-yl)phenyl)-1-(2-hydroxy-2-methylpropyl)-5-methyl-3-oxo-2-phenyl-2,3-dihydro-1H-pyrazole-4-carboxamide. MS (ESI pos. ion) m/z=497 (MH+). Calc'd mass for $C_{28}H_{28}FN_6O_3$: 496.57

EXAMPLE 9

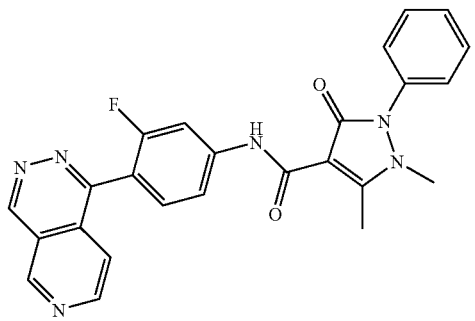

N-(3-fluoro-4-pyrido[3,4-d]pyridazin-1-ylphenyl)-1,5-dimethyl-3-oxo-2-phenyl-2,3-dihydro-1H-pyrazole-4-carboxamide. MS (ESI pos. ion) m/z=455 (MH+). Calc'd mass for $C_{31}H_{30}FN_4O_3$: 454.46

EXAMPLE 10

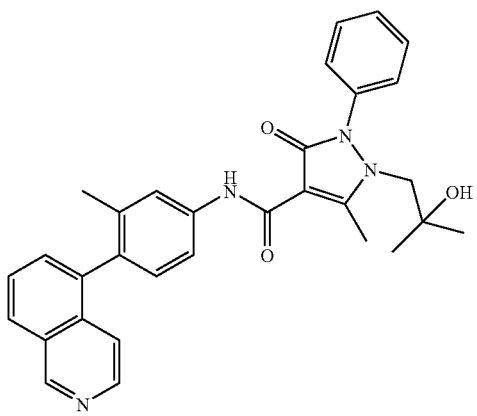

1-(2-Hydroxy-2-methylpropyl)-N-(4-(5-isoquinolinyl)-3-methylphenyl)-5-methyl-3-oxo-2-phenyl-2,3-dihydro-1H-pyrazole-4-carboxamide. A sealable tube was charged with PdCl$_2$(dppf)-CH$_2$Cl$_2$ adduct (0.013 g, 0.016 mmol), isoquinolin-5-ylboronic acid (0.057 g, 0.33 mmol), N-(4-bromo-3-methylphenyl)-1-(2-hydroxy-2-methylpropyl)-5-methyl-3-oxo-2-phenyl-2,3-dihydro-1H-pyrazole-4-carboxamide (0.150 g, 0.33 mmol) and 4 mL dioxane. To this mixture, NaHCO$_3$ solution (0.49 ml, 0.98 mmol) was added and the reaction mixture blanket with N$_2$. The vessel was sealed and heated at 80 C for 19 h. The mixture was allowed to cool to rt, filtered through a pad of celite using ethyl acetate as the eluent and the organic layer washed with water, brine, dried over Na$_2$SO$_4$, filtered and evaporated. The mixture was purified via flash chromatography using a mixture of MeOH in EtOAc as the eluent. The title compound was isolated as an off-white solid (80 mg). MS (ESI pos. ion) m/z=507 (MH+). Calc'd mass for $C_{31}H_{30}FN_4O_3$: 506.60. $^1$H NMR (400 MHz, dmso-d$_6$) δ 10.86 (s, 1H), 9.39 (s, 1H), 8.45 (d, J=5.9 Hz, 1H), 8.17 (d, J=8.1 Hz, 1H), 7.74-7.80 (m, 1H), 7.56-7.85 (m, 5H), 7.44-7.50 (m, 1H), 7.37 (d, J=7.7 Hz, 2H), 7.25 (d, J=5.8 Hz, 1H), 7.17 (d, J=8.1 Hz, 1H), 3.31 (s, 2H), 2.82 (s, 3H), 1.95 (s, 3H), 0.98 (s, 6H).

Scheme 2

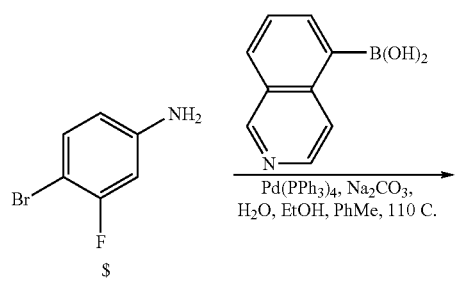

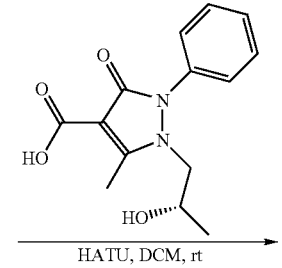

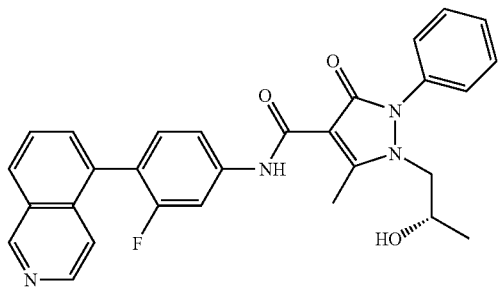

EXAMPLE 11

N-(3-fluoro-4-(isoquinolin-5-yl)phenyl)-1-((S)-2-hydroxypropyl)-5-methyl-3-oxo-2-phenyl-2,3-dihydro-1H-pyrazole-4-carboxamide. 3-fluoro-4-(isoquinolin-5-yl)benzenamine (309.9 mg, 1301 μmol) and (S)-1-(2-hydroxypropyl)-5-methyl-3-oxo-2-phenyl-2,3-dihydro-1H-pyrazole-4-carboxylic acid (359 mg, 1301 μmol) were suspended in DCM (6.5 ml) and DMF (0.65 ml) and hatu (579 mg, 1523 μmol) was added. The reaction was stirred under nitrogen for 5 days, and then filtered. The solid was washed with DCM, and the filtrate was concentrated and purified on silica gel (50:1->40:1->30:1->10:1 DCM/MeOH. The fractions with product were collected, concentrated, treated with MeOH and filtered. The solid was washed with MeOH, collected, and dried under high vacuum to afford the desired N-(3-fluoro-4-(isoquinolin-5-yl)phenyl)-1-((S)-2-hydroxypropyl)-5-methyl-3-oxo-2-phenyl-2,3-dihydro-1H-pyrazole-4-carboxamide (216.0 mg, 435.0 mmol, 33% yield). MS (ESI pos. ion) m/z: 497 (MH+). Calc'd exact mass for $C_{29}H_{25}FN_4O_3$: 496. $^1$H NMR (400 MHz, CDCl$_3$) δ 10.93 (s, 1H), 9.30 (s, 1H), 8.49 (d, J=6.0 Hz, 1H), 8.01 (dd, J=7.0 Hz, 3.0 Hz, 1H), 7.87 (dd, J=12.0 Hz, 2.0 Hz, 1H), 7.71-7.64 (m, 2H), 7.59-7.52 (m, 3H), 7.48 (d, J=8.0 Hz, 1H), 7.42-7.34 (m, 3H), 7.31 (d, J=8.0 Hz, 1H), 4.00-3.83 (m, 2H), 3.72 (dd, J=15.0 Hz, 3.0 Hz, 1H), 2.89 (s, 3H), 1.29-1.24 (m, 1H), 1.11 (d, J=6.0 Hz, 3H).

The compounds of Examples 12 and 13 were prepared using a protocol similar to Example 11:

EXAMPLE 12

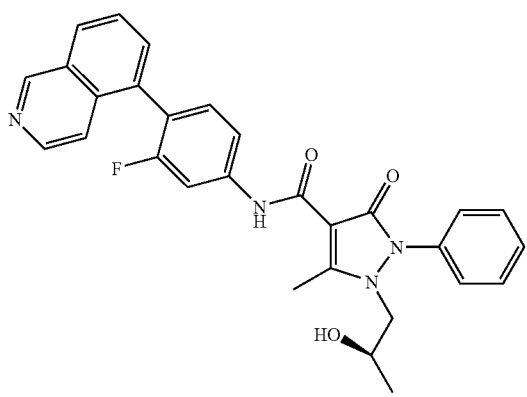

N-(3-fluoro-4-(isoquinolin-5-yl)phenyl)-1-((R)-2-hydroxypropyl)-5-methyl-3-oxo-2-phenyl-2,3-dihydro-1H-pyrazole-4-carboxamide. MS (ESI pos. ion) m/z: 497 (MH+). Calc'd exact mass for $C_{29}H_{25}FN_4O_3$: 496.

EXAMPLE 13

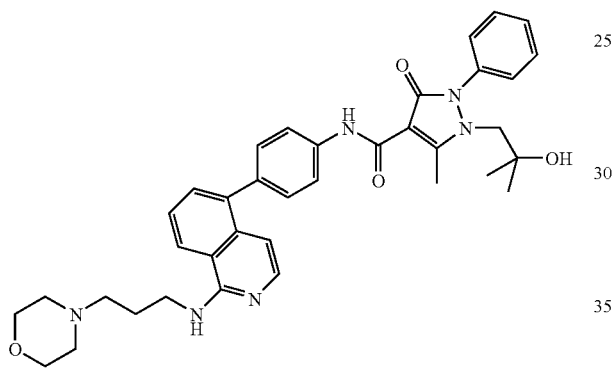

1-(2-hydroxy-2-methylpropyl)-5-methyl-N-(4-(1-(3-morpholinopropylamino)-isoquinolin-5-yl)phenyl)-3-oxo-2-phenyl-2,3-dihydro-1H-pyrazole-4-carboxamide. MS (ESI pos. ion) m/z: 635 (MH+). Calc'd exact mass for $C_{37}H_{42}N_6O_4$: 634. $^1$H NMR (300 MHz, CDCl$_3$) δ 10.76 (s, 1H), 9.23 (s, 1H), 8.66 (d, J=8.18 Hz, 1H), 7.63-7.75 (m, 4H), 7.34-7.51 (m, 4H), 7.20-7.26 (m, 3H), 7.08 (d, J=7.31 Hz, 1H), 3.79-4.0 (m, 10H), 3.32 (s, 4H), 2.83 (s, 3H), 2.36 (s, 2H), 1.08 (s, 6H)

EXAMPLE 14

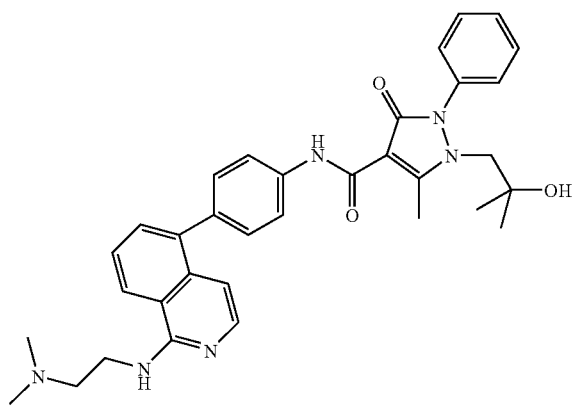

N-(4-(1-(2-(dimethylamino)ethylamino)isoquinolin-5-yl)phenyl)-1-(2-hydroxy-2-methylpropyl)-5-methyl-3-oxo-2-phenyl-2,3-dihydro-1H-pyrazole-4-carboxamide. 5-Bromo-N-(2-(dimethylamino)ethyl)isoquinolin-1-amine (0.068 g, 0.2 mmol) was added to a microwave vial equipped with a stirbar, along with 1-(2-hydroxy-2-methylpropyl)-5-methyl-3-oxo-2-phenyl-N-(4-(4,4,5,5-tetramethyl-1,3,2-dioxaborolan-2-yl)phenyl)-2,3-dihydro-1H-pyrazole-4-carboxamide (0.2 g, 0.3 mmol). Then 1,4-Dioxane (3 ml, 35 mmol) was added into the mixture, followed by 2M K$_2$CO$_3$ (0.5 ml). Then Fibrecat (2.93% Pd, 0.010 g) was added to the mixture. The vial was capped, then placed into CEM Microwave for 10 minutes at 120° C. with 80 Watts of power supplied through Powermax feature. The mixture was diluted with DCM and water, then collected the organic layer by extracting with DCM (3×10 ml). Combined organics, dried over Na$_2$SO$_4$, filtered and concentrated in-vacuo. The crude was purified by ISCO Amino-propyl chromatography using MeOH/DCM as the eluent. This gave the title compounds as a tan amorphous solid (85 mg). MS (ESI pos. ion) m/z: 579 (MH+). Calc'd exact mass for $C_{34}H_{38}N_6O_3$: 578.

The compounds of Examples 15 and 16 were prepared using a protocol similar to Example 14:

EXAMPLE 15

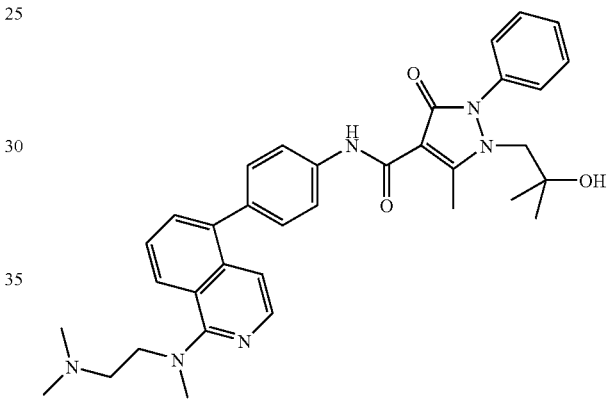

N-(4-(1-((2-(dimethylamino)ethyl)(methyl)amino)isoquinolin-5-yl)phenyl)-1-(2-hydroxy-2-methylpropyl)-5-methyl-3-oxo-2-phenyl-2,3-dihydro-1H-pyrazole-4-carboxamide. MS (ESI pos. ion) m/z: 593 (MH+). Calc'd exact mass for $C_{35}H_{40}N_6O_3$: 592.

EXAMPLE 16

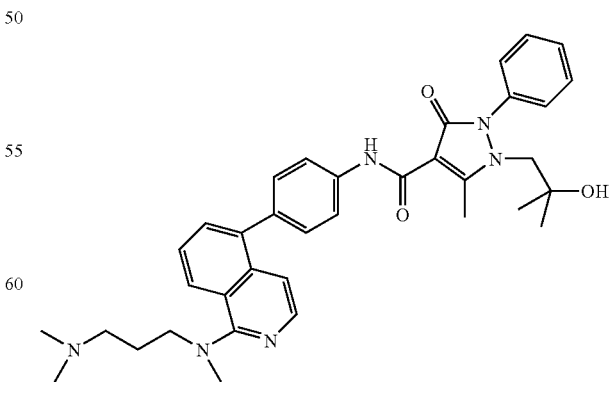

N-(4-(1-((3-(dimethylamino)propyl)(methyl)amino)isoquinolin-5-yl)phenyl)-1-(2-hydroxy-2-methylpropyl)-5-methyl-3-oxo-2-phenyl-2,3-dihydro-1H-pyrazole-4-carboxamide. MS (ESI pos. ion) m/z: 607 (MH+). Calc'd exact mass for $C_{36}H_{42}N_6O_3$: 606.

EXAMPLE 17

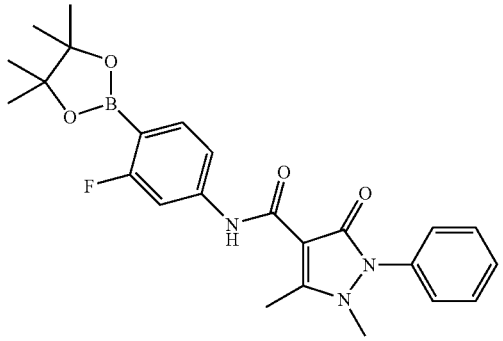

N-(3-fluoro-4-(4,4,5,5-tetramethyl-1,3,2-dioxaborolan-2-yl)phenyl)-1,5-dimethyl-3-oxo-2-phenyl-2,3-dihydro-1H-pyrazole-4-carboxamide. A 75 mL sealable tube was charged with $Pd_2dba_3$ (0.0453 g, 0.0495 mmol), 2-(Dicyclohexylphosphino)-2',4',6'-tri-i-propyl-1,1'-biphenyl (0.0943 g, 0.198 mmol), 4,4,5,5-tetramethyl-2-(4,4,5,5-tetramethyl-1,3,2-dioxaborolan-2-yl)-1,3,2-dioxaborolane (0.905 g, 3.56 mmol), N-(4-bromo-3-fluorophenyl)-1,5-dimethyl-3-oxo-2-phenyl-2,3-dihydro-1H-pyrazole-4-carboxamide (0.800 g, 1.98 mmol), potassium acetate (0.388 g, 3.96 mmol) and 6 mL dioxane and blanked with $N_2$. The vessel was sealed and heated at 80 C for 16 h.

The mixture was allowed to cool to rt, diluted with 40 mL EtOAc, washed with water and brine. The organic layer was dried over $Na_2SO_4$, filtered and evaporated. The mixture was purified via flash chromatography using a gradient of EtOAc in DCM as the eluent. The title compound was collected as a tan solid (815 mg). MS (ESI pos. ion) m/z: 452 (MH+). Calc'd exact mass for $C_{24}H_{27}BFN_3O_4$: 451.

The compounds of Examples 18 and 19 were prepared using a protocol similar to Example 17:

EXAMPLE 18

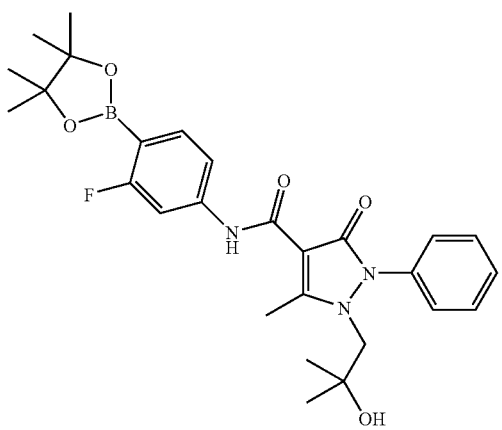

N-(3-fluoro-4-(4,4,5,5-tetramethyl-1,3,2-dioxaborolan-2-yl)phenyl)-1-(2-hydroxy-2-methylpropyl)-5-methyl-3-oxo-2-phenyl-2,3-dihydro-1H-pyrazole-4-carboxamide.

EXAMPLE 19

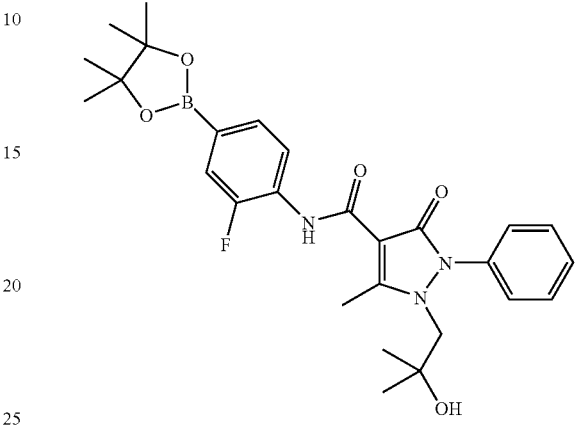

N-(2-Fluoro-4-(4,4,5,5-tetramethyl-1,3,2-dioxaborolan-2-yl)phenyl)-1-(2-hydroxy-2-methylpropyl)-5-methyl-3-oxo-2-phenyl-2,3-dihydro-1H-pyrazole-4-carboxamide.

EXAMPLE 20

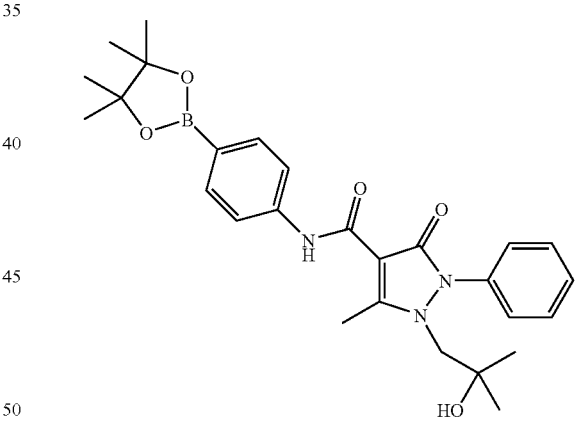

1-(2-Hydroxy-2-methylpropyl)-5-methyl-3-oxo-2-phenyl-N-(4-(4,4,5,5-tetramethyl-1,3,2-dioxaborolan-2-yl)phenyl)-2,3-dihydro-1H-pyrazole-4-carboxamide. A flask was charged with 1-(2-hydroxy-2-methylpropyl)-5-methyl-3-oxo-2-phenyl-2,3-dihydro-1H-pyrazole-4-carboxylic acid (0.500 g, 1.72 mmol), 4-(4,4,5,5-tetramethyl-1,3,2-dioxaborolan-2-yl)benzenamine (0.377 g, 1.72 mmol), $K_2CO_3$ (0.476 g, 3.44 mmol), HATU (0.982 mg, 2.58 mmol) and $CH_2Cl_2$ (10 mL) and the mixture stirred at rt for 14 h. The mixture was diluted with $CHCl_3$ (100 mL), washed with water and sat. $NaHCO_3$. The organic layer was dried over $Na_2SO_4$, filtered and evaporated. The title compound was obtained as a white solid (873 mg). MS (ESI pos. ion) m/z: 492 (MH+). Calc'd exact mass for $C_{27}H_{34}BN_3O_5$: 491.

The compounds of Examples 21-24 were prepared using a protocol similar to Example 20:

EXAMPLE 21

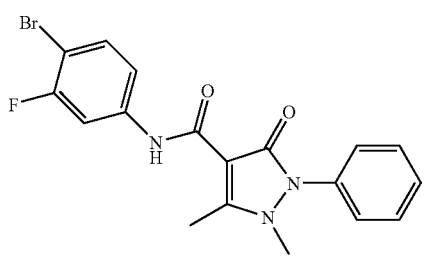

N-(4-bromo-3-fluorophenyl)-1,5-dimethyl-3-oxo-2-phenyl-2,3-dihydro-1H-pyrazole-4-carboxamide. MS (ESI pos. ion) m/z: 404 (MH+). Calc'd exact mass for $C_{18}H_{15}BrFN_3O_2$: 404.

EXAMPLE 22

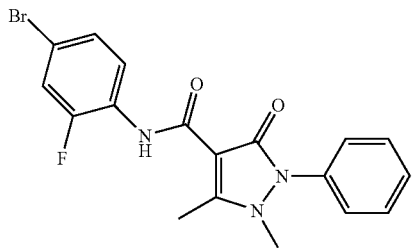

N-(4-bromo-2-fluorophenyl)-1,5-dimethyl-3-oxo-2-phenyl-2,3-dihydro-1H-pyrazole-4-carboxamide. MS (ESI pos. ion) m/z: 404 (MH+). Calc'd exact mass for $C_{18}H_{15}BrFN_3O_2$: 404.

EXAMPLE 23

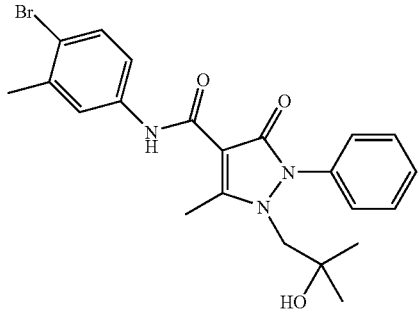

N-(4-bromo-3-methylphenyl)-1-(2-hydroxy-2-methyl-propyl)-5-methyl-3-oxo-2-phenyl-2,3-dihydro-1H-pyrazole-4-carboxamide. MS (ESI pos. ion) m/z: 458 (MH+). Calc'd exact mass for $C_{22}H_{24}BrN_3O_3$: 458.

EXAMPLE 24

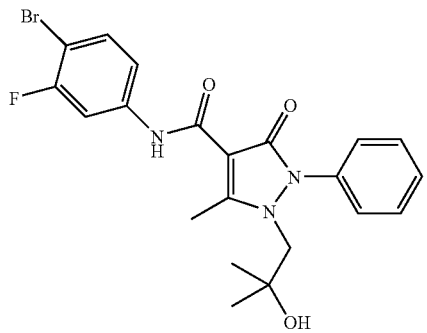

N-(4-bromo-3-fluorophenyl)-1-(2-hydroxy-2-methylpropyl)-5-methyl-3-oxo-2-phenyl-2,3-dihydro-1H-pyrazole-4-carboxamide.

Scheme 3

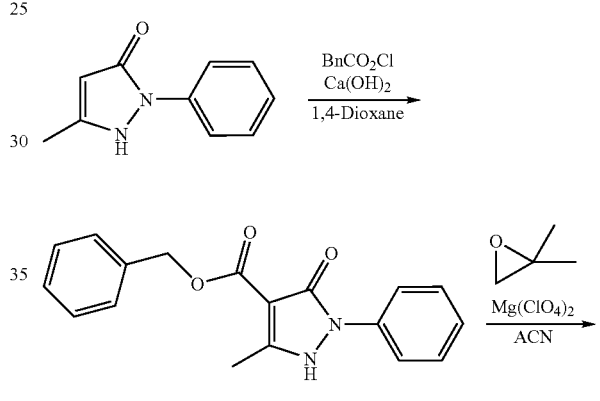

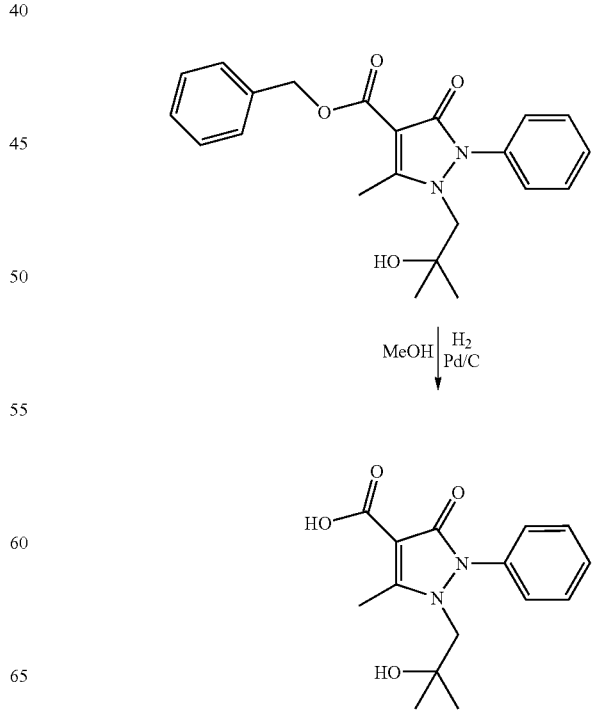

EXAMPLE 25

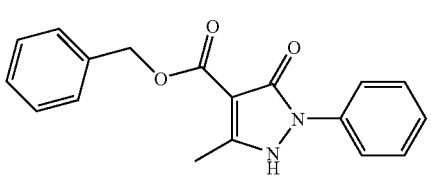

Benzyl 5-methyl-3-oxo-2-phenyl-2,3-dihydro-1H-pyrazole-4-carboxylate. A suspension of 3-methyl-1-phenyl-1H-pyrazol-5-ol (10.0 g, 57 mmol) and calcium hydroxide (8.5 g, 115 mmol) in dry 1,4-dioxane (100 mL) was heated to 50° C. for 20 min. The suspension was chilled to 10° C. and benzyl chloroformate (8.2 ml, 57 mmol) was in dioxane (10 mL) added. The resultant was heated to 90° C. for 3h, cooled to 25° C. and then, chilled (0° C.) 1 M HCl (200 mL) was added. The mixture was stirred at 25° C. overnight. A solid collected by filtration was washed with cold EtOH (2×25 mL) and ether (50 mL), dried at 80° C. (sand bath) exposed to air for 4h to give the title compound (14.0 g, 79% yield) as an off-white solid. MS (ESI pos. ion) m/z: 309 (MH+). Calc'd exact mass for $C_{18}H_{16}N_2O_3$ 308.

EXAMPLE 26

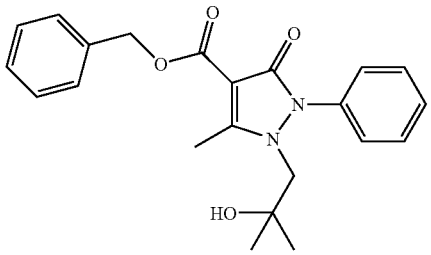

Benzyl 1-(2-hydroxy-2-methylpropyl)-5-methyl-3-oxo-2-phenyl-2,3-dihydro-1H-pyrazole-4-carboxylate. To a stirring suspension of benzyl 5-hydroxy-3-methyl-1-phenyl-1H-pyrazole-4-carboxylate (3380 mg, 1 mmol) in chlorobenzene (30 mL) at 10° C. under nitrogen was added trimethylaluminum (16 mL, 33 mmol, 2M in toluene). Internal temperature reached 27° C. At 25° C., 1,2-epoxy-2-methylpropane (1000 mg, 16 mmol) was added. The reaction mixture was stirred for 3 h at 25° C., and then diluted with THF (500mL). The resultant was chilled to 10° C., and sodium sulfate decahydrate (2g) was added. After 1hr, another 2 g of sodium sulfate decahydrate added. After 2 h, the gel was filtered through a bed of celite and washed with EtOAc (3×100mL). The filterate was then washed with aq. 1M HCl (50mL) and brine. The organic layer was dried over MgSO4. and concentrated. The residue was purified on 120 g silica chromatography (30>90% EtOAc/hex). To give the title compound (1.11 g, 27% yield) as an amorphous solid. MS (ESI pos. ion) m/z: 381 (MH+). Calc'd exact mass for $C_{22}H_{24}N_2O_4$ 380.

EXAMPLE 27

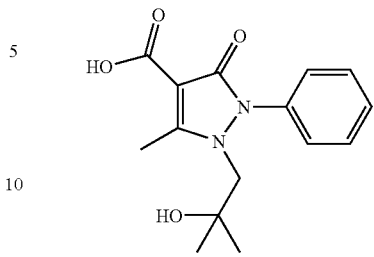

1-(2-hydroxy-2-methylpropyl)-5-methyl-3-oxo-2-phenyl-2,3-dihydro-1H-pyrazole-4-carboxylic acid. To a stirring solution of benzyl 1-(2-hydroxy-2-methylpropyl)-5-methyl-3-oxo-2-phenyl-2,3-dihydro-1H-pyrazole-4-carboxylate (300 mg, 789 μmol) in MeOH (10 mL) was purged with argon for 10 min. To this solution was added Pd/C (40 mg), and the mixture was stirred for 3h under balloon of hydrogen. Reaction was monitored by LCMS. The reaction mixture was filtered through a bed of celite and concentrated under reduced pressure to give the title compound (220 mg, 96.1% yield) as an off-white solid. MS (ESI pos. ion) m/z: 291 (MH+). Calc'd exact mass for $C_{15}H_{18}N_2O_4$ 290.

The compounds of Example 28 and 29 were prepared using a protocol similar to Example 27:

EXAMPLE 28

(S)-1-(2-hydroxypropyl)-5-methyl-3-oxo-2-phenyl-2,3-dihydro-1H-pyrazole-4-carboxylic acid. MS (ESI pos. ion) m/z: 277 (MH+). Calc'd exact mass for $C_{14}H_{16}N_2O_4$: 276.

EXAMPLE 29

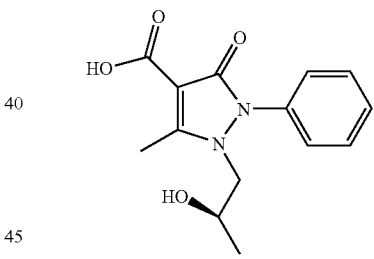

(R)-1-(2-hydroxypropyl)-5-methyl-3-oxo-2-phenyl-2,3-dihydro-1H-pyrazole-4-carboxylic acid. MS (ESI pos. ion) m/z: 277 (MH+). Calc'd exact mass for $C_{14}H_{16}N_2O_4$: 276.

EXAMPLE 30

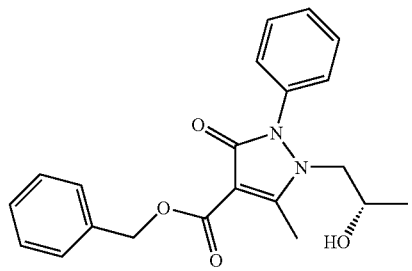

(S)-1-(2-hydroxypropyl)-5-methyl-3-oxo-2-phenyl-2,3-dihydro-1H-pyrazole-4-carboxylic acid. To a 500 mL roundbottomed flask was added benzyl 5-methyl-3-oxo-2-phenyl-2,3-dihydro-1H-pyrazole-4-carboxylate (3.1 g, 10 mmol), chlorobenzene (30 mL) and the mixture cooled in an ice bath. The trimethylaluminum (25 ml, 50 mmol) was added and the ice bath removed followed by the addition of (S)-2-methyloxirane (0.87 g, 15 mmol). The mixture stirred 1 h and cooled in an ice bath with the addition of THF (60 mL). Sodium sulfate decahydrate (3g) was added to the mixture cautiously (foaming) and the mixture stirred 1 h. Sodium sulfate (10 g) was added and stirred 1 h. The mixture was filtered through celite, washed with 4:1 chloroform/isopropanol and the filtrate concentrated, diluted with chloroform, washed with 1 N HCl and sat. sodium bicarbonate. The organic layer was dried over sodium sulfate and concentrated. The crude product was purified by silica gel chromatography eluting with methanol/chloroform to afford the title compound as a foam (1.5 g). MS (ESI pos. ion) m/z: 367 (MH+). Calc'd exact mass for $C_{21}H_{22}N_2O_4$: 366.

The compound of Example 31 was prepared using a protocol similar to Example 30.

EXAMPLE 31

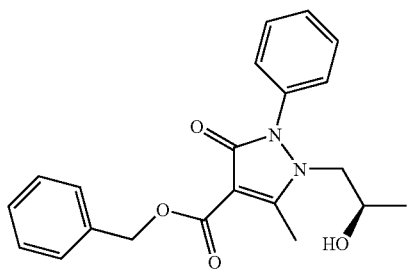

(R)-benzyl 1-(2-hydroxypropyl)-5-methyl-3-oxo-2-phenyl-2,3-dihydro-1H-pyrazole-4-carboxylate.). MS (ESI pos. ion) m/z: 367 (MH+). Calc'd exact mass for $C_{21}H_{22}N_2O_4$: 366.

EXAMPLE 32

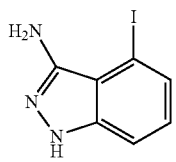

4-Iodo-1H-indazol-3-amine. A mixture of 2-fluoro-6-iodobenzonitrile (5.040 g, 20 mmol), hydrazine hydrate (10 ml, 319 mmol) and n-butanol (100 mL) were heated at 110 C for 5 h and the mixture allowed to cool to rt. The mixture was partitioned between 100 mL EtOAc and 200 mL water and the layers separated. The aqueous layer was extracted with additional EtOAc (25 mL) and combined with organic layer. The combined organic layers were combined and washed with water, brine, dried over $Na_2SO_4$, filtered and evaporate. The title compound was obtained as an off-white solid (5.25 g). $^1$H NMR (400 MHz, dmso-$d_6$) δ 11.79 (s, 1H), 7.34 (d, J=7.2 Hz, 1H), 7.27 (d, J=8.3 Hz, 1H), 6.90-6.95 (m, 1H), 5.04 (s, 2H).

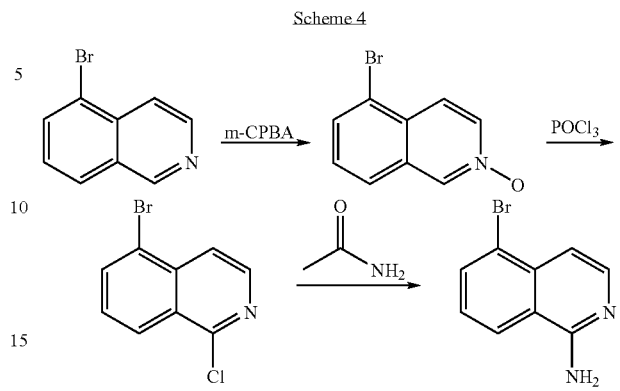

EXAMPLE 33

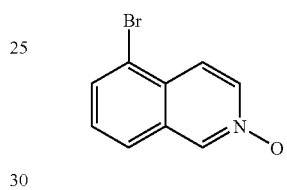

5-bromoisoquinoline-N-oxide. To a solution of 5-bromoisoquinoline (10.65 g, 51.19 mmol) in $CH_2Cl_2$ (250 mL), m-CPBA (9.717 g, 56.31 mmol) was added and the mixture refluxed for 20 h and allowed to cool to rt. The mixture was washed with sat $Na_2SSO_3$ (75 mL), then 3×1N NaOH, then brine. The organic layer was dried w/$Na_2SO_4$, filtered and evaporated. The residue was crystallized from $CH_2Cl_2$: $Et_2O$ to yield the title compound as a white fluffy solid (4.58 g). MS (ESI pos. ion) m/z: 224 (MH+). Calc'd exact mass for $C_9H_5BrNO$: 224.

EXAMPLE 34

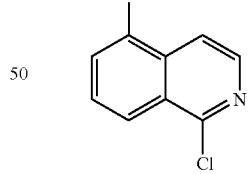

5-Bromo-1-chloroisoquinoline. To a solution of 5-bromoisoquinoline-N-oxide (4.56 g, 20.4 mmol) in 100 mL $CH_2Cl_2$, phosphorus oxychloride (4.17 ml, 44.8 mmol) was added and the mixture heated at 45 C for 4 h. The mixture was allowed to cool and evaporated. Water and ice were added alternating, portion-wise and $CH_2Cl_2$ was added to the mixture. The organic layer was made pH 14 with 1 M NaOH, and the organic layer washed with sat. $NaHCO_3$, dried over $Na_2SO_4$, filtered and evaporated. The solid was triturated with methanol and the title compound collected as a fluffy off-white solid (3.93 g). MS (ESI pos. ion) m/z: 242 (MH+). Calc'd exact mass for $C_9H_5BrClN$: 242.

EXAMPLE 35

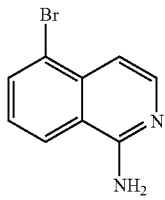

5-Bromoisoquinolin-1-amine. Acetamide (4.9 g, 82 mmol), 5-bromo-1-chloroisoquinoline (1.00 g, 4.1 mmol) and $K_2CO_3$ (2.8 g, 21 mmol) were combined in a sealed tube and the mixture heated at 200 C for 1.5 h. The mixture was allowed to cool to rt and the solid residue suspended in 400 mL water. The brown solid was collected as the title compound (750 mg). MS (ESI pos. ion) m/z: 223 (MH+). Calc'd exact mass for $C_9H_7BrN_2$: 223.

EXAMPLE 36

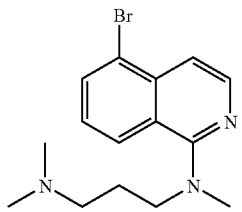

5-Bromo-N-(3-(dimethylamino)propyl)-N-methylisoquinolin-1-amine. 5-Bromo-1-chloroisoquinoline (0.2 g, 0.8 mmol) was added to a microwave vial, along with Pyridine (3 ml, 37 mmol) with stirbar. Then N,N,N''-trimethyl-1,3-propanediamine (0.32 ml, 1 mmol) was added into the mixture, while stirring. The vial was placed into CEM microwave for 10 minutes at 100° C., while 80 Watts of power was supplied through powermax feature. The mixture was diluted with DCM and water and extracted organic layer with DCM (3×10 ml). The combined organic extracts were dried over $Na_2SO_4$, filtered and concentrated in-vacuo. The crude material was purified by ISCO Amino-propyl silica-gel chromatography using MeOH/DCM as the eluent. This gave a tan amorphous solid after drying under high-vac, which was titled product (65 mg). MS (ESI pos. ion) m/z: 324 (MH+). Calc'd exact mass for $C_{15}H_{20}BrN_3$: 322.

The compounds of Examples 37-39 were prepared using a protocol similar to Example 36:

EXAMPLE 37

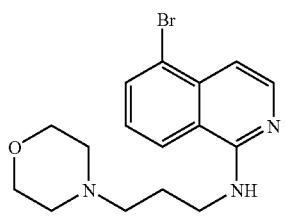

5-Bromo-N-(3-morpholinopropyl)isoquinolin-1-amine

EXAMPLE 38

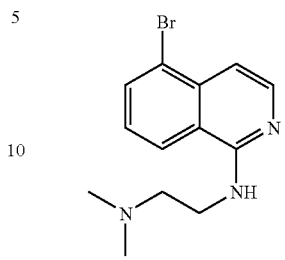

5-Bromo-N-(2-(dimethylamino)ethyl)isoquinolin-1-amine. MS (ESI pos. ion) m/z: 294 (MH+). Calc'd exact mass for $C_{13}H_{16}BrN_3$: 294.

EXAMPLE 39

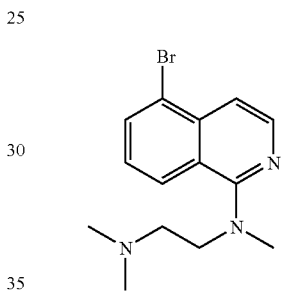

5-Bromo-N-(2-(dimethylamino)ethyl)-N-methylisoquinolin-1-amine. MS (ESI pos. ion) m/z: 310 (MH+). Calc'd exact mass for $C_{14}H_{18}BrN_3$: 308.

EXAMPLE 40

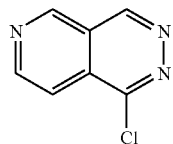

1-Chloropyrido[3,4-d]pyridazine. A flask was charged with pyrido[3,4-d]pyridazin-1-ol (0.080 g, 0.54 mmol) (see Brzezinski, J. Z.; Bzowski, H. B.; Epsztajin, J. *Tetrahedron*, 1996, 52, 3261-72) and phosphorus oxybromide (0.62 g, 2.2 mmol) and heated at 80 C 2:30pm. Solid still stuck to walls of flask so 3 mL $POCl_3$ was added and refluxed 4 h and the mixture concentrated in-vacuo. The mixture was quenched with ice and sat $NaHCO_3$ and the brown solid collected. The solid is a mixture of the title compound and 1-bromopyrido[3,4-d]pyridazine (22 mg). MS (ESI pos. ion) m/z: 166 (MH+). Calc'd exact mass for $C_7H4ClN_3$: 165.

EXAMPLE 41

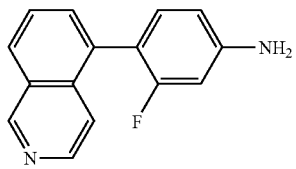

3-Fluoro-4-(isoquinolin-5-yl)benzenamine. 4-Bromo-3-fluorobenzenamine (2.51 g, 13 mmol) and 5-isoquinolineboronic acid (4.23 g, 24 mmol) were suspended in toluene (35 ml) and EtOH (35 ml) and tetrakis(triphenylphosphine)palladium (812 mg, 0.70 mmol) was added, followed by 10% aqueous sodium carbonate (40 ml). The flask was fitted with a reflux condenser and placed in a preheated oil bath (110 C) and stirred under nitrogen for 4 hours. The reaction was then cooled to room temperature, partially concentrated, and diluted with water. The aqueous phase was extracted with DCM, and the organic extracts were combined, dried over sodium sulfate, filtered, concentrated, and purified on silica gel (50:1->30:1->20:1 DCM/MeOH). The fractions with product were collected, concentrated, and washed with DCM and hexanes. The remaining solid was dried under high vacuum to afford the desired 3-fluoro-4-(isoquinolin-5-yl)benzenamine (2.568 g, 10.78 mmol, 94% purity, 82% yield). MS (ESI pos. ion) m/z: 497 (MH+). Calc'd exact mass for $C_{15}H_{11}FN_2$: 239. $^1$H NMR (400 MHz, CDCl$_3$): 9.30 (s, 1H), 8.50 (dd, J=6.0 Hz, 2.0 Hz, 1H), 8.02-7.96 (m, 1H), 7.68-7.63 (m, 2H), 7.58-7.54 (m, 1H), 7.16 (dt, J=8.0 Hz, 2.0 Hz, 1H), 6.61 (dt, J=8.0 Hz, 2.0 Hz, 1H), 6.56 (dt, J=11.5 Hz, 2.0 Hz, 1H), 3.93 (br s, 2H).

The compound of Example 42 was prepared using a protocol similar to Example 41:

EXAMPLE 42

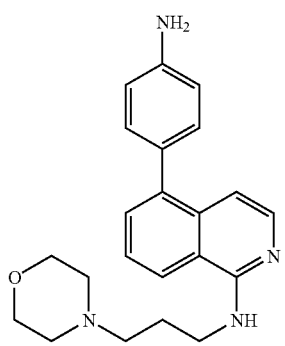

5-(4-aminophenyl)-N-(3-morpholinopropyl)isoquinolin-1-amine

Biological Testing

The efficacy of the compounds of the invention as inhibitors of HGF related activity is demonstrated as follows.

c-Met Receptor Assay

Cloning, Expression and Purification of c-Met Kinase Domain

A PCR product covering residues 1058-1365 of c-Met (c-Met kinase domain) is generated as described in WO 06/116,713 the entirety of which is incorporated herein by reference.

Alternative purification of human GST-cMET from Baculovirus cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche (#10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant OD$_{280}$ readings are run on another 12% Tris Glycine gel. The peak tubes with GST-cMET are pooled and the OD$_{280}$ is read with the column buffer listed above as the blank buffer.

Phosphorylation of the purified GST-cMET is performed by incubating the protein for 3 h at RT with the following:

| concentration | Final |
|---|---|
| a) 100 mM ATP (Sigma #A7699) | 25 mM |
| b) 1.0 M MgCl$_2$ (Sigma #M-0250) | 100 mM |
| c) 200 mM Sodium Orthovanadate (Sigma #S-6508) | 15 mM |
| d) 1.0 M Tris-HCl, pH 7.00 (in house) | 50 mM |
| e) H$_2$0 | |
| f) GST-cMET | 0.2-0.5 mg/mL |

After incubation, the solution is concentrated in a Vivaspin 20 ml Concentrator to a volume less than 2.00 ml. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the OD$_{280}$ is read with the column buffer used as the blank.

A Kinase reaction Buffer is prepared as follows:

|  |  |  | Per 1 L |
|---|---|---|---|
| 60 mM HEPES $_p$H 7.4 | 1 M stock | 16.7 X | 60 mL |
| 50 mM NaCl | 5 M stock | 100 X | 10 mL |
| 20 mM MgCl$_2$ | 1 M stock | 50 X | 20 mL |
| 5 mM MnCl$_2$ | 1 M stock | 200 X | 5 mL |

When the assay is carried out, freshly add:

| 2 mM DTT | 1 M stock | 500 X |
|---|---|---|
| 0.05% BSA | 5% stock | 100 X |
| 0.1 mM Na$_3$OV$_4$ | 0.1 M stock | 1000 X |

The HTRF Buffer Contains:

50 mM Tris-HCl (pH 7.5), 100 mM NaCl, 0.1% BSA, 0.05% Tween 20,5mM EDTA

Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:

0.1 nM final Eu-PT66
11 nM final SA-APC

Methods:

1. Dilute GST-cMet (P) Enzyme in Kinase Buffer as Follows:

Prepare 8 nM GST-cMet (P) working solution (7.32 μM to 8 nM, 915×, 10 μL to 9.15 mL). In a 96 well clear plate [Costar #3365] add 100 μL in eleven columns, in one column add 100 μL kinase reaction buffer alone.

2. Assay Plate Preparation:

Use Biomek FX to transfer 10 μL 8 nM GST-cMet (P) enzyme, 48.4 μL kinase reaction buffer, 1.6 μL compound (in DMSO) (Start concentration at 10 mM, 1 mM and 0.1 mM, sequential dilution 1:3 to reach 10 test points) in a 96 well costar clear plate [Costar # 3365], mix several times. Then incubate the plate at RT for 30 min.

3. Prepare Gastrin and ATP working solution in kinase reaction buffer as follows:

Prepare 4 μM Gastrin and 16 μM ATP working solution

|  |  | Per 10 mL |
|---|---|---|
| Gastrin 4 μM stock | (500 μM to 4 μM, 125 X) | 80 μL |
| ATP 16 μM stock | (1000 μM to 16 μM, 62.5 X) | 160 μL |

Use Biomek FX to add 20 μl ATP and Gastrin working solution to the assay plate to start reaction, incubate the plate at RT for 1 h.

4. Transfer 5 μL reaction product at the end of 1 h into 80 μL HTRF buffer in black plate

[Costar # 3356], read on Discover after 30 min incubation.

Assay Condition Summary:

| $K_M$ ATP * | 6 μM |
|---|---|
| [ATP] | 4 μM |
| $K_M$ Gastrin/p(EY) | 3.8 μM |
| [gastrin] | 1 μM |
| [enzyme] | 1 nM |

$K_M$ ATP, $K_M$ gastrin for various enzymes were determined by HTRF/$^{33}$P labeling and HTRF methods.

c-Met Cell-Based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. $2\times10^4$ cells in medium were plated per well in a 96 well plate and incubated at 37° C. overnight. The cells were serum-starved by replacing the growth media with basic medium (DMEM low glucose+0.1 BSA, 120 μL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 μL per well) were diluted with basic medium (240 μL) in a 96 well plate. The cells were washed once with basic medium (GIBCO, DMEM 11885-076) then compound solution was added (100 μL). The cells were incubated at 37° C. for 1 h. A (2 mg/mL) solution of CHO-HGF (7.5 μL) was diluted with 30 mL basic medium to provide a final concentration of 500 ng/mL. This HGF-containing media (120 μL) was transferred to a 96 well plate. Compounds (1.2 μL) was added to the HGF-containing media and mixed well. The mixture of media/HGF/compound (100 μL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 μL, Roche Protease inhibitor (Complete, # 1-697-498) 2 tablets, Phosphatase Inhibitor II (Sigma, #P-5726) 200 μL, and a sodium vanadate solution (containing 900 μL PBS, 100 μL 300 mM NaVO$_3$, 6 μL H$_2$O$_2$ (30% stock) and stirred at RT for 15 min) (90 μL). The cells were washed once with ice cold 1×PBS (GIBCO, #14190-136), then lysis buffer (60 μL) was added and the cells were incubated on ice for 20 min.

The IGEN assay was performed as follows: Dynabeads M-280 streptavidin beads were pre-incubated with biotinylated anti-human HGFR (240 μL anti-human-HGFR (R&D system, BAF527 or BAF328)@100 μg/mL+360 μL Beads (IGEN #10029+5.4 μL buffer—PBS/1% BSA/0.1% Tween20) by rotating for 30 min at RT. Antibody beads (25 μL) were transferred to a 96 well plate. Cell lysate solution (25 μL) was transferred added and the plate was shaken at RT for 1 h. Anti-phosphotyrosine 4G10 (Upstate 05-321) (19.7 μL antibody+6 mL 1×PBS) (12.5 μL) was added to each well, then incubated for 1 h at RT. Anti-mouse IgG ORI-Tag (ORIGEN #110087) (24 μL Antibody+6 mL buffer) (12.5 μL) was added to each well, then incubated at RT for 30 min. 1×PBS (175 μL) was added to each well and the electrochemiluminescence was read by an IGEN M8. Raw data was analyzed using a 4-parameter fit equation in XLFit.

rHu-bFGF: Stock concentration of 180 ng/μL: R&D rHu-bFGF: Added 139 μL of the appropriate vehicle above to the 25 μg vial lyophilized vial. 13.3 μL of the [180 ng/μL] stock vial and added 26.6 μL of vehicle to yield a final concentration of 3.75 μM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control.

Tumor Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control The compounds exemplified herein have been assayed and inhibit c-Met. Illustrative activity values are provided in the following table.

| Ex. | cMet $K_i$ (µM) |
|---|---|
| 1 | 0.021 |
| 2 | 0.028 |
| 3 | 0.056 |
| 4 | 0.073 |
| 5 | 0.085 |
| 6 | 0.142 |
| 7 | 0.156 |
| 8 | 0.252 |
| 9 | 2.382 |
| 10 | 0.373 |
| 11 | 0.047 |
| 12 | 0.062 |
| 13 | 3.288 |
| 14 | >20 |
| 15 | >6.67 |
| 16 | 1.448 |

Formulations

Also embraced within this invention is a class of pharmaceutical compositions comprising the active compounds of Formula I, II and III in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:
1. A compound of the following Formula I, II or III.

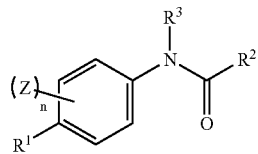

I

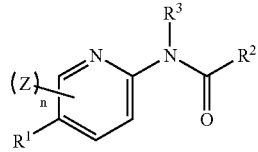

II

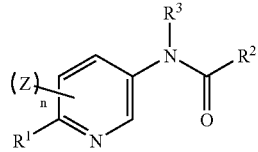

III enantiomers, diastereomers, and salts thereof
wherein
$R^1$ is an aryl ring system or a 5-14-membered nitrogen containing heteroaryl or heterocyclyl ring system; any of which may be optionally independently substituted with 1 to 4 Z groups;
$R^2$ is

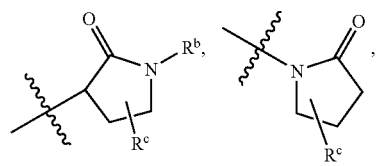

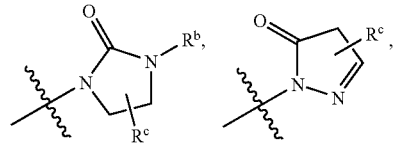

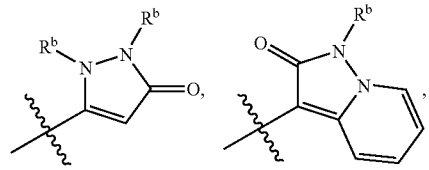

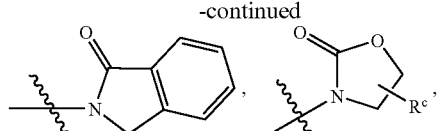

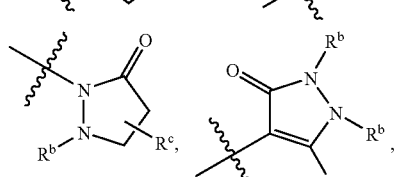

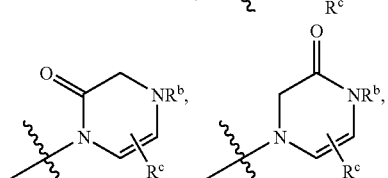

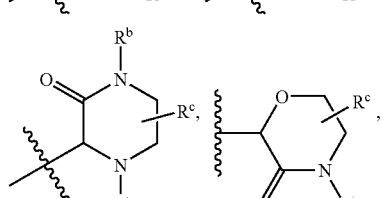

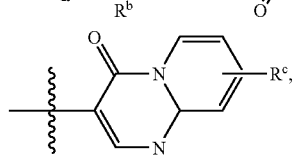

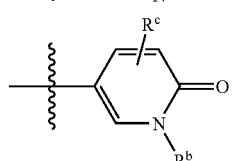

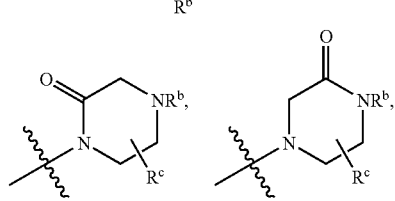

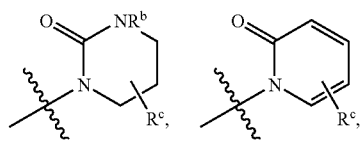

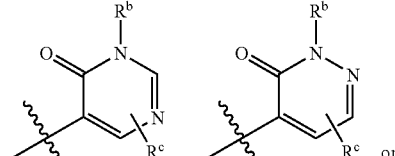

or

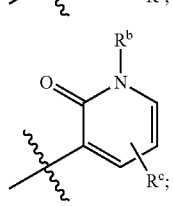

;

R³ is hydrogen or alkyl optionally substituted with one or more Z groups;

R$^b$ is independently selected at each occurrence from
  a) H, or
  b) $C_{1-6}$alkyl, $C_{3-6}$cycloalkyl, $C_{6-10}$ aryl, $C_{6-10}$ aryl-$C_{1-3}$ alkyl, $C_{5-10}$ heteroaryl, $C_{5-10}$ heteroaryl-$C_{1-3}$ alkyl, 5-6 membered heterocyclyl or 5-6-membered heterocyclyl-$C_{1-3}$ alkyl, any of which may be optionally substituted with one or more Z groups;

R$^c$ is selected from
  a) H, halo, hydroxy or
  b) $C_{1-6}$alkyl, $C_{3-6}$cycloalkyl, $C_{3-6}$cycloalkyl$C_{1-6}$alkyl, $C_{1-6}$alkoxy, $C_{1-6}$ alkyoxy$C_{1-6}$alkyl, hydroxy-$C_{1-6}$alkyl, $C_{6-10}$ aryl, $C_{6-10}$ aryl-$C_{1-3}$ alkyl, $C_{5-10}$ heteroaryl, $C_{5-10}$ heteroaryl-$C_{1-3}$ alkyl, 5-6 membered heterocyclyl, 5-6-membered heterocyclyl-$C_{1-3}$ alkyl, R$^d$R$^e$N— or R$^d$R$^e$N—$C_{1-3}$ alkyl, any of which may be optionally substituted with one or more Z groups;

R$^d$ is selected from
  a) H, or
  b) $C_{1-6}$alkyl, $C_{3-6}$cycloalkyl, $C_{3-6}$cycloalkyl$C_{1-6}$alkyl, $C_{1-6}$alkyoxy$C_{1-6}$alkyl, hydroxy-$C_{1-6}$alkyl, $C_{6-10}$ aryl-$C_{1-3}$ alkyl, $C_{5-10}$ heteroaryl-$C_{1-3}$ alkyl, or 5-6-membered heterocyclyl-$C_{1-3}$ alkyl, any of which may be optionally substituted with one or more Z groups;

R$^e$ is selected from
  a) H or
  b) $C_{1-6}$alkyl, $C_{6-10}$ aryl-$C_{1-3}$ alkyl, 5-6 membered heterocyclyl-$C_{1-2}$-alkyl, 5-6-membered heterocyclyl; $C_{6-10}$ aryl, $C_{5-10}$ heteroaryl, or $C_{5-10}$ heteroaryl-$C_{1-3}$ alkyl, any of which may be optionally substituted with one or more Z groups;

or when R$^d$ and R$^e$ are bonded to the same nitrogen atom, they may optionally combine to form a heterocyclyl ring, Z is an optional substituent independently selected at each occurrence from
  a*) halo, nitrile, hydroxy, alkoxy, aryloxy, heteroaryloxy; heterocylyloxy, cycloalkyloxy, aralkyloxy, heteraralkyloxy, heterocyclylalkoxy, cycloalkylalkoxy, —NR$^b$R$^b$, —NR$^b$—C(=O)R$^b$, —NR$^b$—C(=O) OR$^b$, —NR$^b$—C(=O)—NR$^b$R$^b$, C(=O)—NR$^b$R$^b$, —C(=O)OR$^b$; —S(O$_2$)—NR$^b$R$^b$, —NR$^b$—(SO$_2$)R$^b$, —S(O$_2$)R$^b$, and —S(O)R$^b$; or
  b*) alkyl, alkenyl, alkynyl, cycloalkyl, aryl, aralkyl, heteroaryl, heteroaralkyl, heterocyclyl, and heterocyclylalkyl, any of which may be optionally substituted with one or more of the substituents listed in the above section a*; and n is an integer from zero to three.

2. A compound of claim 1 wherein R² is or a pharmaceutically acceptable salt thereof.

3. A compound of claim 2 wherein R² is

R$^b$ at each occurrence is independently $C_{1-6}$alkyl, $C_{1-6}$hydroxyalkyl, $C_{1-6}$alkoxyalkyl, $C_{6-10}$ aryl, or $C_{6-10}$ aryl-$C_{1-3}$ alkyl; and R$^c$ is $C_{1-6}$alkyl, or a pharmaceutically acceptable salt thereof.

4. A compound of claim 1 wherein R¹ is

-continued
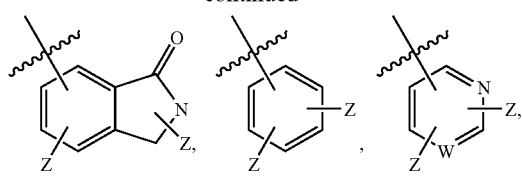
where W is C or N; and
V is C, O or N,
or a pharmaceutically acceptable salt thereof.
5. A compound of claim 3 wherein $R^1$ is
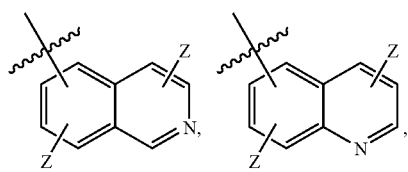
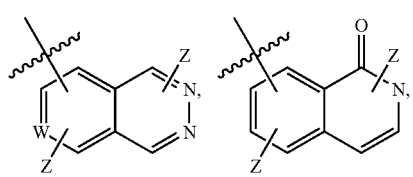
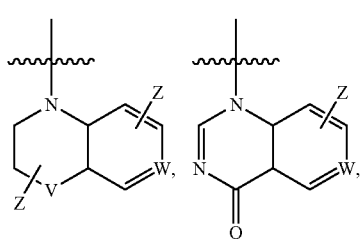
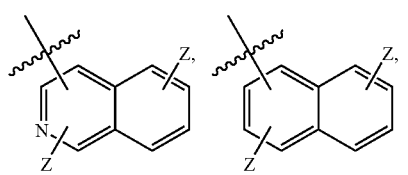
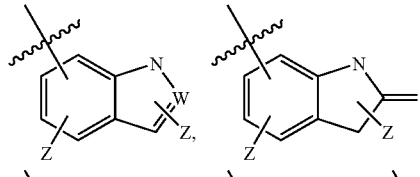
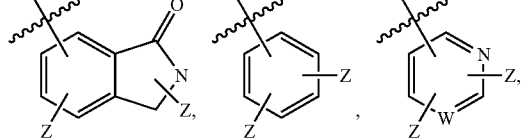
where W is C or N; and
V is C, O or N,
or a pharmaceutically acceptable salt thereof.
6. A compound of claim 5 wherein $R^1$ is
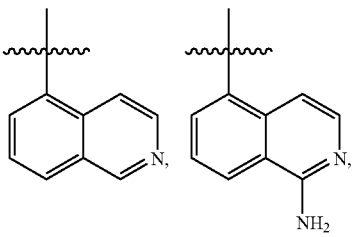
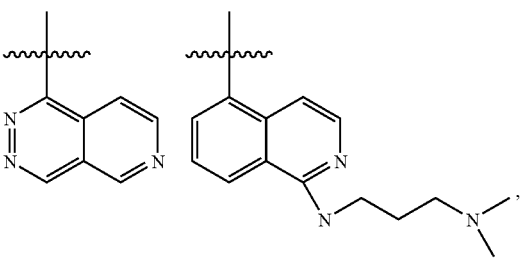
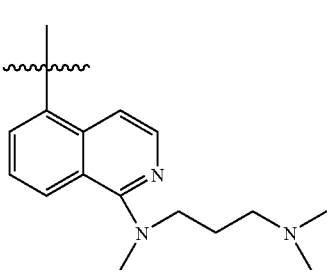
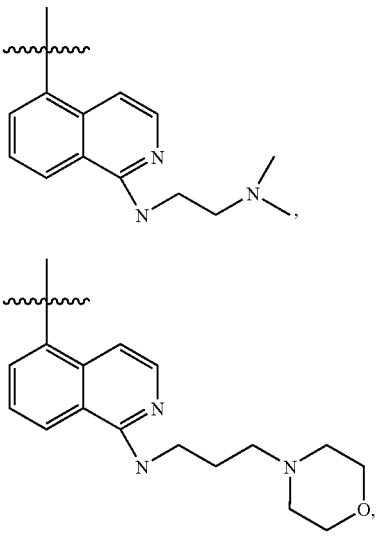
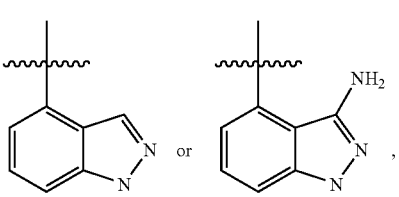
or a pharmaceutically acceptable salt thereof.

7. A compound of claim 5 wherein R² is
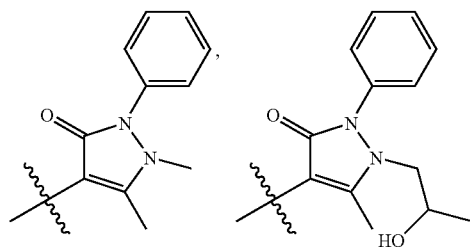
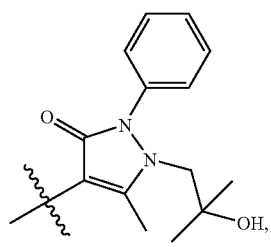
or a pharmaceutically acceptable salt thereof.
8. A compound of claim 6 wherein R² is
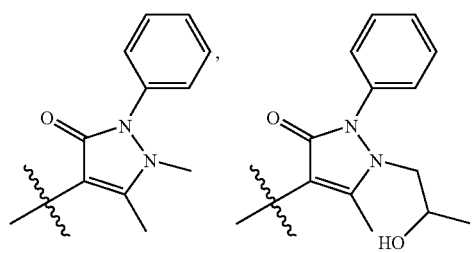
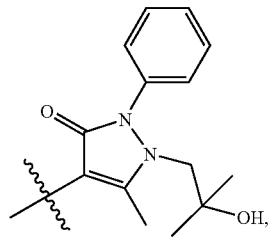
or a pharmaceutically acceptable salt thereof.
9. A compound of claim 8 selected from
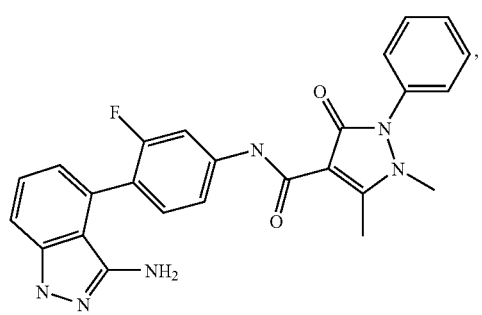
-continued
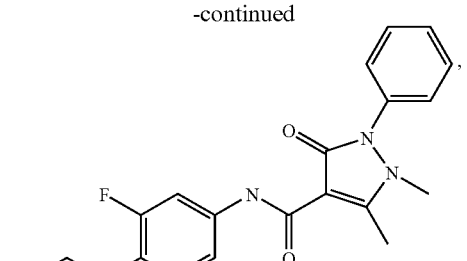
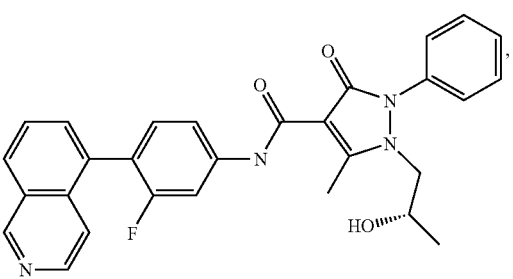
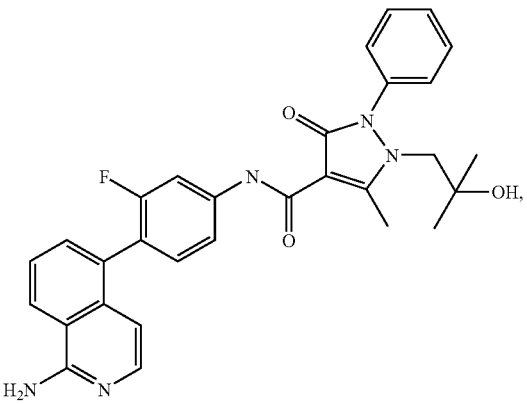
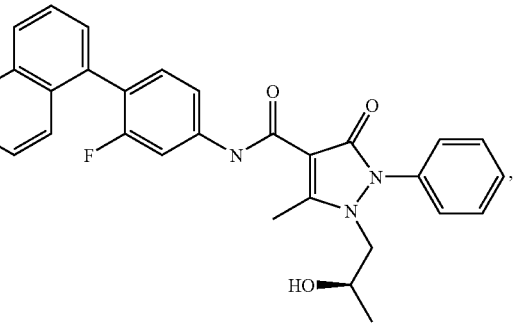

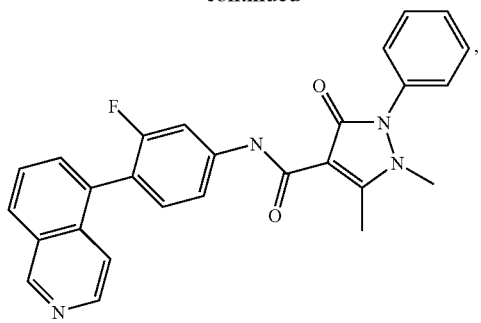
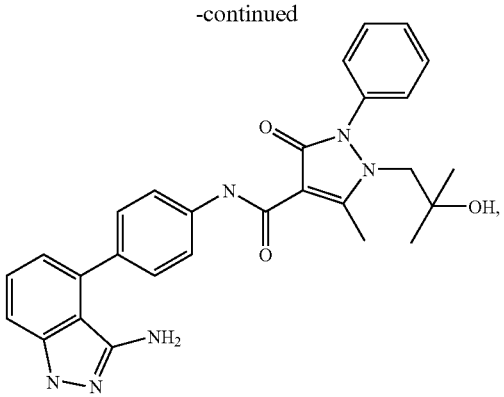

-continued

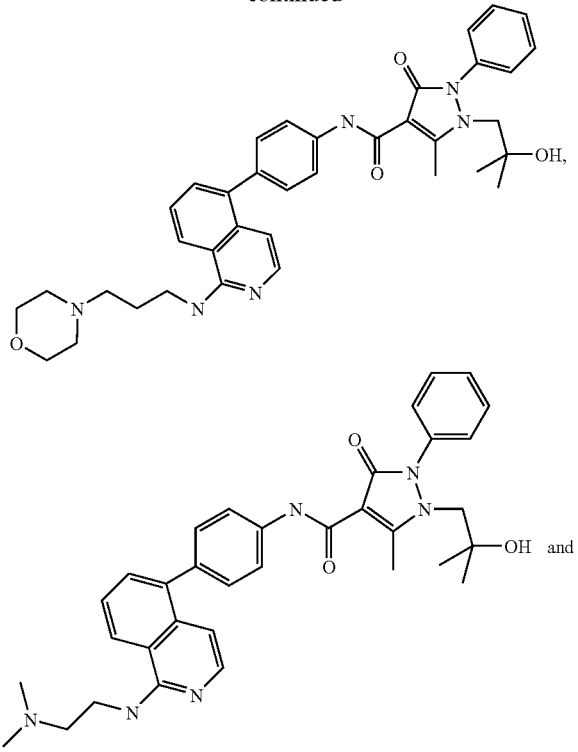

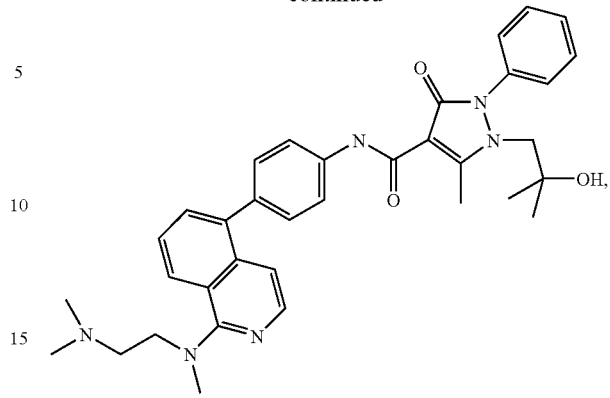

or a pharmaceutically acceptable salt thereof.

10. A pharmaceutical composition comprising a pharmaceutically-acceptable carrier and a compound of claim 1.

11. A method of treating glioma in a subject comprising administering an effective amount of a compound of claim 1 or a pharmaceutically acceptable salt thereof.

12. A method of treating adencarcinoma in a subject comprising administering an effective amount of a compound of claim 1 or a pharmaceutically acceptable salt thereof.

* * * * *